(12) United States Patent  
Turzi

(10) Patent No.: US 12,678,550 B2  
(45) **Date of Patent: \*Jul. 14, 2026**

(54) STANDARDIZATIONS AND MEDICAL DEVICES FOR THE PREPARATION OF PLATELET RICH PLASMA (PRP) OR BONE MARROW CONCENTRATE (BMC) ALONE OR IN COMBINATION WITH HYALURONIC ACID

(71) Applicant: RegenLab USA LLC, Brooklyn, NY (US)

(72) Inventor: Antoine Turzi, Mollens (CH)

(73) Assignee: REGEN LAB USA LLC, New York, NY (US)

( * ) Notice: Subject to any disclaimer, the term of this patent is extended or adjusted under 35 U.S.C. 154(b) by 1059 days.

This patent is subject to a terminal disclaimer.

(21) Appl. No.: 17/353,787

(22) Filed: Jun. 21, 2021

(65) Prior Publication Data

US 2021/0346587 A1 Nov. 11, 2021

Related U.S. Application Data

(63) Continuation of application No. 15/529,415, filed as application No. PCT/EP2015/077853 on Nov. 26, 2015, now Pat. No. 11,077,241.

(30) Foreign Application Priority Data

Nov. 26, 2014 (GB) ...................................... 1421013

(51) Int. Cl.  
*A61M 1/38* (2006.01)  
*A61J 1/20* (2006.01)  
(Continued)

(52) U.S. Cl.  
CPC .............. *A61M 1/38* (2013.01); *A61J 1/2089* (2013.01); *A61K 35/16* (2013.01); *A61K 35/28* (2013.01);  
(Continued)

(58) Field of Classification Search  
CPC ......... A61K 35/16; A61M 1/029; A61M 1/38; A61M 1/3672; A61J 1/2089; A61J 1/2013  
See application file for complete search history.

(56) References Cited

U.S. PATENT DOCUMENTS 3,852,194 A 12/1974 Zine, Jr.  
4,101,422 A 7/1978 Lamont et al.  
(Continued)

FOREIGN PATENT DOCUMENTS

CA 2181462 C 6/1996  
EP 2361644 B1 8/2011  
(Continued)

OTHER PUBLICATIONS

"Autologous PRP" RegenLab, May 2, 2006, pp. 1-2. https://web.archive.org/web/20060502171522/http://www.regenkit.com/products.html.

(Continued)

*Primary Examiner* — Leslie R Deak

(74) *Attorney, Agent, or Firm* — Rahman LLC

(57) ABSTRACT

The present invention is related to the field of tissue regeneration. It concerns more particularly new standardizations and medical devices for the preparation of A-PRP, PRP, BMC, fat tissue, alone or in combination with a biomaterial or cell extract.

31 Claims, 12 Drawing Sheets

Automatic transfer  
by vacuum in tube  
containing biomaterial

(51) Int. Cl.

| | | |
|---|---|---|
| *A61K 35/16* | (2015.01) | |
| *A61K 35/28* | (2015.01) | |
| *A61M 1/02* | (2006.01) | |
| *A61M 1/36* | (2006.01) | |
| *A61B 17/34* | (2006.01) | |
| *A61K 35/35* | (2015.01) | |

(52) U.S. Cl.
CPC .......... *A61M 1/029* (2013.01); *A61M 1/3672* (2013.01); *A61B 17/34* (2013.01); *A61J 1/2013* (2015.05); *A61K 35/35* (2013.01); *A61M 2202/0415* (2013.01); *A61M 2202/08* (2013.01); *A61M 2202/10* (2013.01)

(56) References Cited

U.S. PATENT DOCUMENTS

| | | | |
|---|---|---|---|
| 4,148,764 A | 4/1979 | Lamont et al. | |
| 4,190,535 A | 2/1980 | Luderer et al. | |
| 4,350,593 A | 9/1982 | Kessler | |
| 5,236,604 A | 8/1993 | Fiehler | |
| 5,459,030 A | 10/1995 | Lin | |
| 5,906,744 A | 5/1999 | Carroll et al. | |
| 6,020,196 A | 2/2000 | Hu et al. | |
| 6,979,307 B2 | 12/2005 | Beretta et al. | |
| 11,077,241 B2 * | 8/2021 | Turzi ........................ | A61P 1/02 |
| 2002/0187130 A1 | 12/2002 | Kindness et al. | |
| 2005/0170327 A1 | 8/2005 | Sumida et al. | |
| 2005/0205498 A1 | 9/2005 | Sowemimo-Coker et al. | |
| 2015/0037436 A1 | 2/2015 | Huang et al. | |
| 2015/0306288 A1 * | 10/2015 | Delorme ............. | A61M 1/0272 435/307.1 |
| 2016/0235889 A1 | 8/2016 | Pallotta et al. | |
| 2017/0028137 A1 | 2/2017 | Mirabito et al. | |
| 2017/0065638 A1 | 3/2017 | Fraser | |

FOREIGN PATENT DOCUMENTS

| | | | | | |
|---|---|---|---|---|---|
| WO | 2003095974 A2 | 11/2003 | | | |
| WO | 2010122548 A2 | 10/2010 | | | |
| WO | 2011110948 A2 | 9/2011 | | | |
| WO | WO-2013061309 A2 * | 5/2013 | ........... | A61K 31/722 |
| WO | 2013111130 A1 | 8/2013 | | | |
| WO | WO-2014057220 A1 * | 4/2014 | ........... | A01N 1/0263 |

OTHER PUBLICATIONS

"BD Vacutainer CPT—Cell Preparation Tube with Sodium Citrate", Beckton, Dickinson and Co., (2003), pp. 1-14.

"BD Vacutainer Tube Guide", Beckton, Dickinson and Co., published 2006, pp. 1-8. http://www.bd.com/resource.aspx?IDX=11068.

"Regen Lab: Products for Tissue Repair", Regan Lab, May 2, 2006, 2 pages. https://web.archive.org/web/20070713152626/http://www.regenkit.com/company.html.

"RegenPRP-Kit Medical Device lla CE1250", Regenlab Geneve, Sep. 26, 2004, pp. 1-17 https://web.archive.org/web/20050313100219/http://www.regenkit.com/docs/Regen PRP-Kit_ang.pdf.

2003 Swiss Assoc. for Quality and Management Systems, IQNet certificate, Risk analysis, contract, pp. 1-34.

Arkin, et al: "Tubes and Additives for Venous Blood Specimen Collection; Approved Standard—Fifth Edition ", NCCLS document H1-A5, 940 West Valley Road, Suite 1400, Wayne, Pennsylvania 19087-1898 USA; 2003, vol. 23, No. 33, pp. 1-44.

De Oliveira, et al., "An overview about erythrocyte membrane", Clinical Hemorheology and Microcirculation, Institute of Molecular Medicine, Lisbon, Portugal, published 2010, vol. 44, pp. 63-74.

Du Toit, et al.: "Soft and hard-tissue augmentation with platelet-rich plasma: Tissue culture dynamics, regeneration and molecular biology perspective", International Journal of Shoulder Surgery, published 2007, vol. 1, pp. 64-73.

Everts, et al.: "Platelet rich plasma and platelet gel, A review.", Journal of Extra-Corporeal Technology, Orlando FL, USA, published May 18, 2006, vol. 38, pp. 25-59.

Gadol, et al.: "A new method for separating mononuclear cell from whole blood" Diagnostic Immunology, published 1985; vol. 3, Issue No. 3, pp. 145-154 https://www.ncbi.nlm.nih.gov/pubmed/3931958.

Garratty, et al.: "Red Cell Antigens as Functional Molecules and Obstacles to Transfusion, Part I. Erythrocyte Blood Group Antigens: Physiologic and Pathologic Functions of Red Cell Antigen-Bearing Molecules", by Marilyn J. Teien. Hematology American Society of Hematology Education Program, published: 2002, pp. 445-462.

Graziani, et al. "The in vitro effect of different PRP concentrations on osteoblasts and fibroblasts", Clinical Oral Implants Research, published Apr. 2006, vol. 17, issue No. 2, pp. 212-219.

Storry, J., "Review: the function of blood group-specific RBC membrane components", Immunohematology Journal of Blood Group Serology and Education, published 2004, vol. No. 20, issue No. 4, pp. 206-216.

Laurens, I., "Development of a new extraction method for platelet-rich plasma and partial purification of platelet-Derived growth factor and transforming growth factor beta", Dissertation submitted in fulfillment of the requirements for he degree Magister Scientiae in the Dept. of Pharmacology, Faculty of Health Sciences, Univ. of Pretoria, South Africa., published Oct. 2013, pp. 1-148.

Perttila, J., et al.: "Plasma Fibronectin concentrations in blood products", Intensive Care Med., published Jan. 1990, vol. 16, issue No. 1, pp. 41-43; ISSN 1432-1238, https://doi .org/10 .1007 /BF01706323.

Raffoul, et al.: "Impact of platelets concentrate and keratinocyte suspension on wound healing—a prospective randomized trial", The International Journal of Artificial Organs, published 2008, pp. 1-16.

Shoham, N., et al. "The mechanics of hyaluronic acid/adipic acid dihydrazide hydrogel: Towards developing a vessel for delivery of preadipocytes to native tissues," Journal of the Mechanical Behavior of Biomedical Materials vol. 28, Dec. 2013, Abstract only.

Regen Lab Presentation, "Innovation in Biological Tissue Regeneration", 2005, pp. 1-54.

Regen Lab webpage available at www.regenkit.com as of May 16, 2006, 1 page. https://web.archive.org/web/20060516102752/http://www.regenkit.com/regen_THT.html.

Regen Lab webpage available at www.regenkit.com as of Apr. 26, 2006, 1 page. https://web.archive.org/web/20060426121922/http://www.regenkit.com/.

Regen-Kit Instructions for Use, May 2, 2006, pp. 1-2. https://web.archive.org/web/200605021717071522/http:/www.regenkit.com/doc/RegenPRP-Kit-IFU.pdf.

RegenLab Certification from Swiss Association for Quality and Management Systems for the developing and marketing of medical devices, Feb. 21, 2005, and Regen Lab CE Certification "X(1250" for the Regen Kit under Registration No. 2378801, from SQS, Dec. 23, 2003, 2 pages. https://web.archive.org/web/20060511153104/http://www.regenkit.com:80/doc/ReGen%20Lab%20%20ISO%209001%20&%2013485.pdf.

Research Study, Comparison of EmCyte GS30-PurePRP® II, EmCyte GS60—PurePRP® II, Arteriocyte Magellan, Stryker Regenkit®THT, and Eclipse PRP. Principle Investigator Robert Mandie, PhD, Biosciences Research Associates, Cambridge, MA, May 2016, pp. 1-14.

Slichter, et al.: "Platelet Transfusion Therapy", Chapter 14 in "Platelets In Hematologic And Cardiovascular Disorders". Edited by Paolo Gresele et al.; Cambridge University Press, Cambridge United Kingdom, 2008, pp. 242-260.

Translation Swiss 2003 Assoc. and Management Systems, IQNet certificate, Risk analysis, contract, pp. 23-24.

Tsay, et al.:"Differential growth factor retention by platelet-rich plasma composites", Journal of Oral and Maxillofacial Surgery, vol. No. 63, Issue No. 4, 2005, pp. 521-528, ISSN 0278-2391, http://www.sciencedirect.com/science/article/pii/S0278239104016349.

Van Laethem, et al.: "Diagnosis of human immunodeficiency virus infection by a polymerase chain assay evaluated in patents harbouring strains of diverse geographical origin" Journal of Virological Methods, published Feb. 1998, vol. 70, issue 2, pp. 153-166,

(56) References Cited

OTHER PUBLICATIONS

Department of Microbiology & Immunology, Rega Institute for Medical Research & University Hospitals, Leuven, Belgium.

Wiwanitkit, V., "Serum separator tube, a useful application of evacuated blood collection system," Songkla Med J., 2002, 20(4), pp. 301-305.

Kimura, Y., et al: "Adipose tissue engineering based on human preadipocytes combined with gelatin microspheres containing basic fibroblast growth factor", Biomaterials, Elsevier Science Publishers BV., Barking, GB, vol. 24, No. 14, Jun. 1, 2003, Abstract only.

Matsumoto, D., et al: "Cell-assisted lipotransfer: supportive use of human adipose-derived cells for soft tissue augmentation with lipoinjection",Tissue Engineering, Larchmont, NY, US, vol. 12, No. 12, Dec. 18, 2006, Abstract only.

Dohan Ehrenfest D M, et al: "Classification of platelet concentrates: from pure platelet-rich plasma (P-PRP) to leucocyte- and platelet-rich fibrin (L-PRF)", Trends in Biotechnology, Elsevier Publications, Cambridge, GB, vol. 27, No. 3, Mar. 1, 2009, pp. 158-167.

Doi, K., et al: "Enrichment isolation of adipose-derived stem/stromal cells from the liquid portion of liposuction aspirates with the use of an adherent column", Cytotherapy, vol. 16, No. 3, Mar. 1, 2014, Abstract only.

Brandl F., et al: "Enzymatically degradable poly(ethylene glycol) based hydrogels for adipose tissue engineering", Biomaterials, vol. 31, Issue 14, May 2010, Abstract, Introduction, and Figures only, 6 pages.

Zuk P.A., et al: "Human adipose tissue is a source of multipotent stem cells", Molecular Biology of the Cell, American Society for Cell Biology, US, vol. 13, No. 12, Dec. 20, 2002, pp. 4279-4295.

Dong, et al: "In vivo injectable human adipose tissue regeneration by adipose-derived stem cells isolated from the fluid portion of liposuction aspirates", Tissue and Cell, vol. 46, No. 3, Jun. 1, 2014, Abstract only.

Ghorbani, et al: "Isolation of adipose tissue mesenchymal stem cells without tissue destruction: a non-enzymatic method", Tissue and Cell, vol. 46, No. 1, Feb. 1, 2014, Abstract only.

Written Opinion of the International Search Authority, Application No. PCT/EP2015/077853, Issued: Jun. 13, 2016, 16 pages.

NIH, U.S. National Library of Medicine, ClinicalTrials.gov, "Effect of Platelet Rich Plasma and Keratinocyte Suspensions on Wound Healing," Centre Hospitalier Universitaire Vaudois, Mar. 6, 2009, Study Details, Tabular View, Study Results, 26 pages. https://clinicaltrials.gov/ct2/show/study/NCT00856934; https://clinicaltrials.gov/ct2/show/record/NCT00856934; https://clinicaltrials.gov/ct2/show/results/NCT00856934.

Mallory, D., Editor-In-Chief, "Immunohematology", Journal of Blood Group Serology and Education, vol. 20, No. 4, 2004, 61 pages.

* cited by examiner

Plasma supernatant

Cellular sediment

Cell selector gel

Red blood cells

Automatic transfer
by vacuum in tube
containing biomaterial

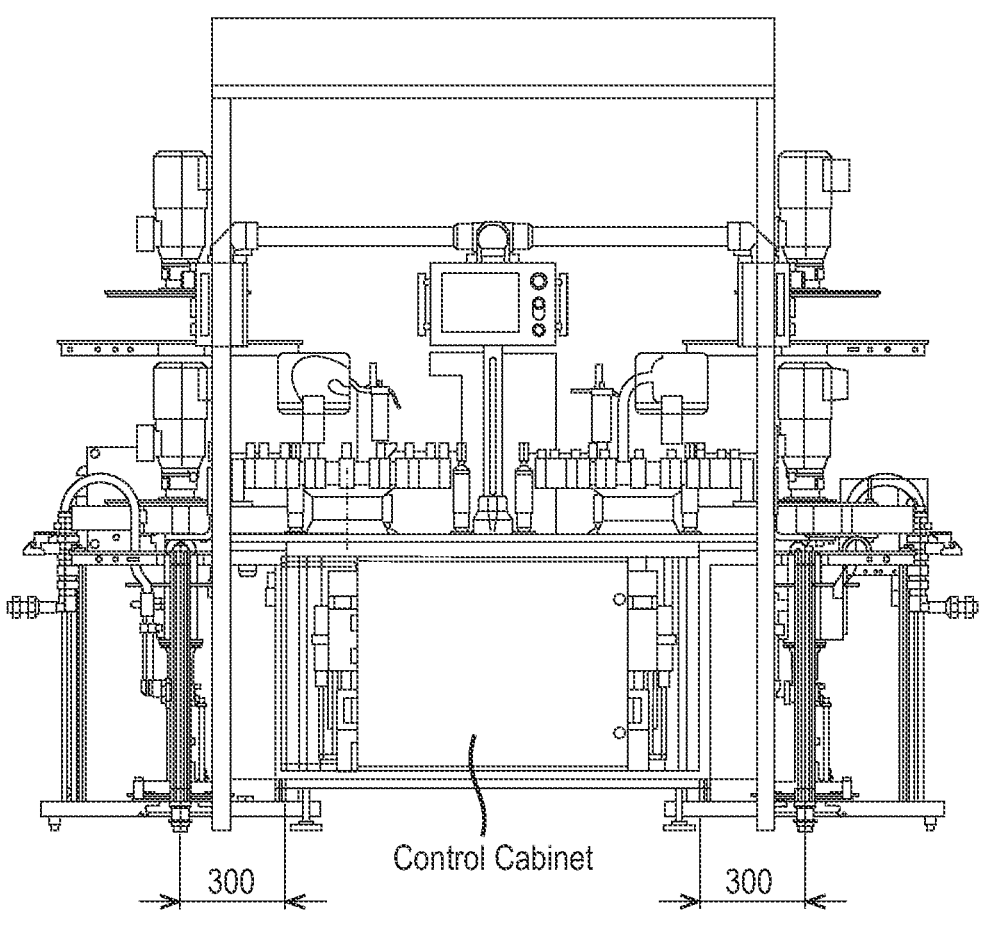
300       Control Cabinet       300
FIG. 6(contd.)
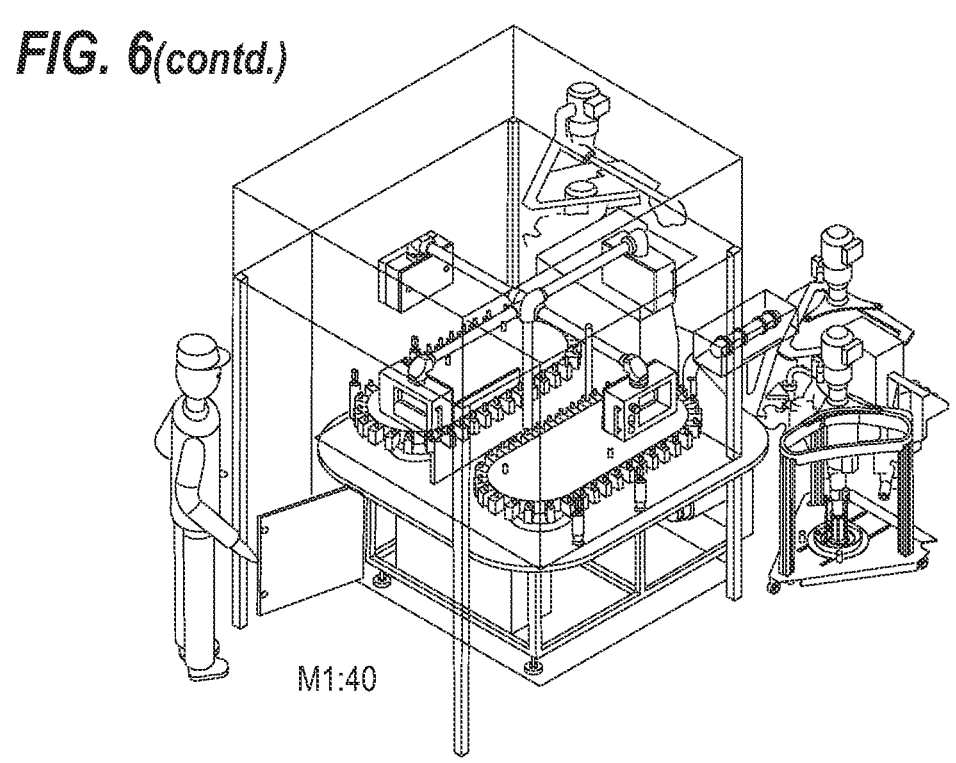
M1:40

*FIG. 6(contd.)*
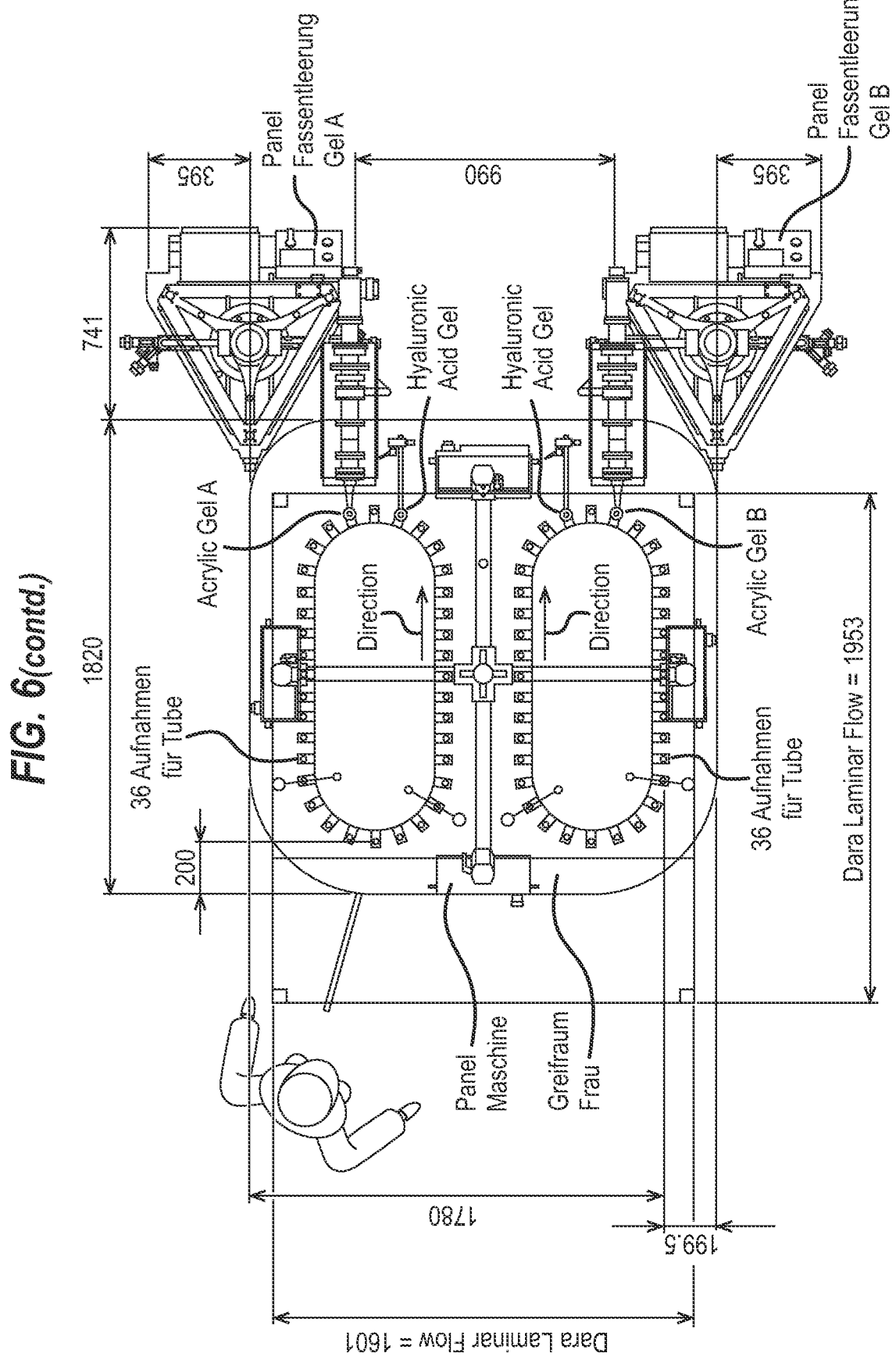

DETAIL B

MAßSTAB 1 : 5

M1:30

FIG. 7(contd.)
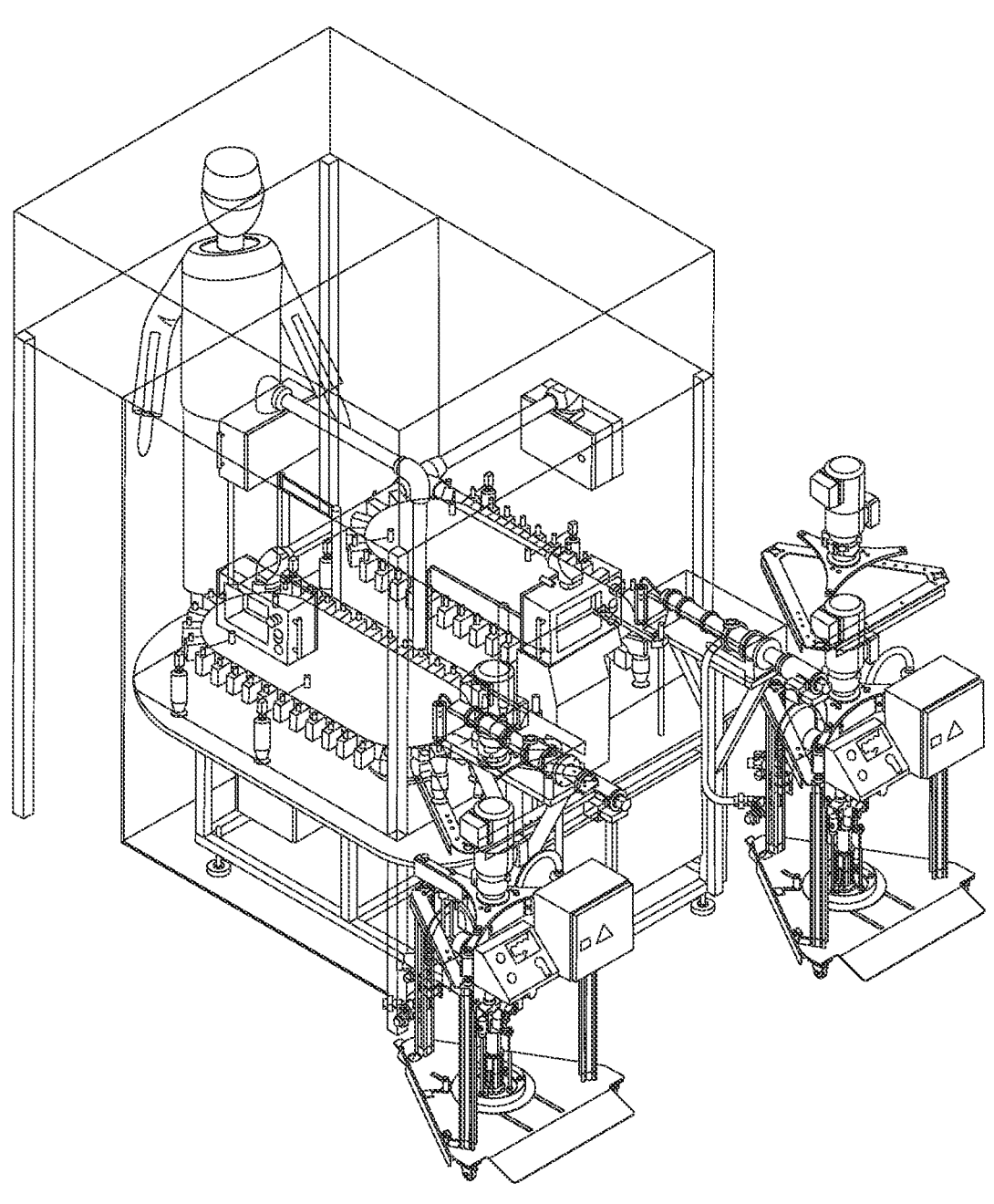

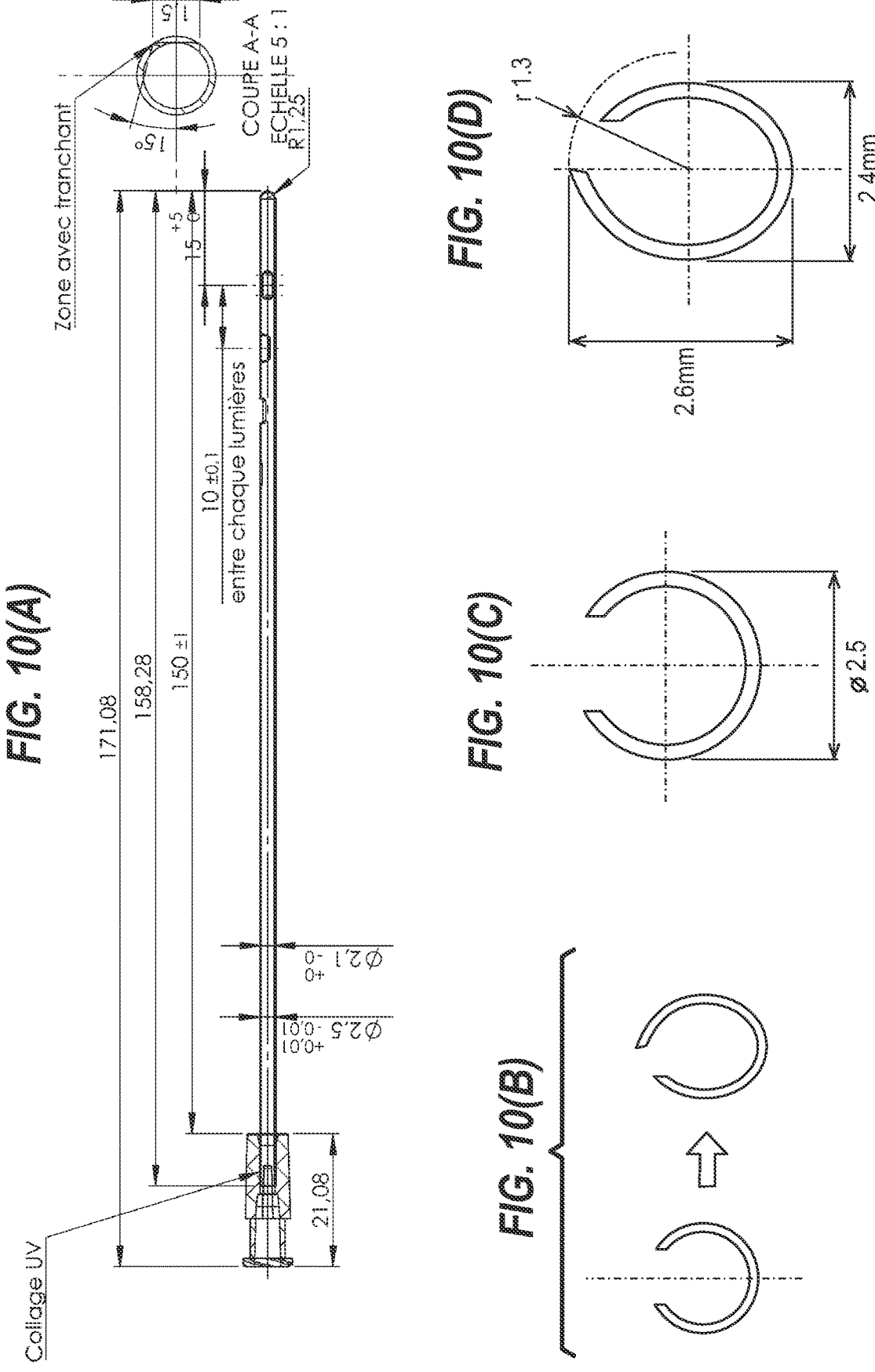

STANDARDIZATIONS AND MEDICAL DEVICES FOR THE PREPARATION OF PLATELET RICH PLASMA (PRP) OR BONE MARROW CONCENTRATE (BMC) ALONE OR IN COMBINATION WITH HYALURONIC ACID

CROSS REFERENCE TO RELATED APPLICATIONS

This application is a continuation of U.S. Ser. No. 15/529,415 filed on May 24, 2017, which is a § 371 application of PCT Serial No. PCT/EP/2015077853 filed on Nov. 26, 2015, which claims priority to Great Britain Application No. 1421013.2 filed on Nov. 26, 2014, the complete disclosures of which, in their entireties, are herein incorporated by reference.

TECHNICAL FIELD

The present invention is related to the field of tissue regeneration. It concerns more particularly new standardizations and medical devices intended for the preparation of PRP, A-PRP, BMC, fat tissue, alone or in combination with a biomaterial or cell extract.

BACKGROUND

Various techniques of preparation of Platelet Rich Plasma (PRP) by centrifugation processes have been developed. However, due to the sensitivity of the platelet cells and the variability of the efficiency of the methods of separation of the platelets from the red blood cells, a great variability exist among the methods used for the preparation of platelet concentrates. There is also an important loss of valuable biologic tissue from the patients when PRP is prepared with old empiric or semi-automatic devices. In addition, in order to obtain platelet concentrates, the use of relatively complex kits and costly dedicated machinery and the equally costly involvement of specialized technicians are required.

Therefore there is a need for the development of hematology tubes with pharmaceutical grade standards, enabling a safe collection of blood, depletion of all erythrocytes and preparation of plasma cells with high yields of platelets and leukocytes, easy to use and cost effective. There is also a need for the development of medical devices enabling the preparation of PRP in combination with other compositions like cell extracts or biomaterials, possibly in large quantities.

Further, there is a need in the development of new machines for hematological tubes for the manufacturing of pharmaceutical grade standards and with constant, predictable and reliable biological results.

SUMMARY

The invention relates to the field of tissue regeneration. It concerns more particularly new standardizations, tubes and medical devices for thrombin, platelet concentrate and wound healant preparations, compositions, PRP or A-PRP compositions, BMC or A-BMC compositions and uses thereof.

In a first aspect, the invention provides a container for the preparation of a Bone Marrow Concentrate (BMC) and/or Plasma Concentrate (PC), characterized in that said container (1) comprises or is prefilled with:

i) at the least one anticoagulant, and/or ii) at the least one filter and/or composition allowing separation of red blood cells (RBCs).

In a second aspect, the invention provides a container for the preparation of PC and/or BMC in combination with at the least one biomaterial preferably or optionally selected from hyaluronic acid, chitosan, silk protein or fibroin, cell extract or any combination thereof, characterized in that said container comprises or is prefilled with a biomaterial preferably or optionally selected from hyaluronic acid, chitosan, silk protein or fibroin, cell extract or any combination thereof.

In a third aspect, the invention provides a syringe for the preparation of PC and/or BMC in combination with at the least one biomaterial preferably or optionally selected from hyaluronic acid, chitosan, silk protein or fibroin, cell extract or any combination thereof, characterized in that said syringe comprises or is prefilled with a biomaterial preferably or optionally selected from hyaluronic acid, chitosan, silk protein or fibroin, cell extract or any combination thereof.

In a fourth aspect, the invention provides a medical device or kit consisting of or comprising at the least one container and/or at the least one syringe according to any of the previous aspects.

In a fifth aspect, the invention provides a method for the preparation of a composition, preferably PC and/or BMC optionally in combination with at the least one biomaterial using at least one container and/or syringe according to any of the previous aspects.

In a sixth aspect, the invention provides a composition, preferably PC and/or BMC optionally in combination with at the least one biomaterial, obtained using at least one container and/or syringe according to any of the previous aspects.

In a seventh aspect, the invention provides the use of a composition, method, medical device, kit, container or syringe according to any of the previous claims in therapy, dermatology, dentistry, orthopedics, sports medicine, cosmetics, esthetics, surgery, ophthalmology, mesotherapy, injections, infiltrations, subcutaneous applications, wound care, volume enhancement, volume corrections, mechanical support and/or visco-supplementation.

In further aspects, the invention provides a fat harvesting cannula, a multiple connector device allowing mixing of different substances or compositions, a medical device comprising such cannula and/or multiple connector device, methods using such devices for fat harvesting, fat washing, fat enrichment in closed circuit and uses thereof.

BRIEF DESCRIPTION OF THE DRAWINGS

The accompanying drawings, which are incorporated herein and form a part of the specification illustrate preferred embodiments of the present invention, and together with the description, serve to explain the principles of the invention.

FIGS. 10A to 10D. Schematic view of fat harvesting cannula.

DETAILED DESCRIPTION

Figures 1, 2:
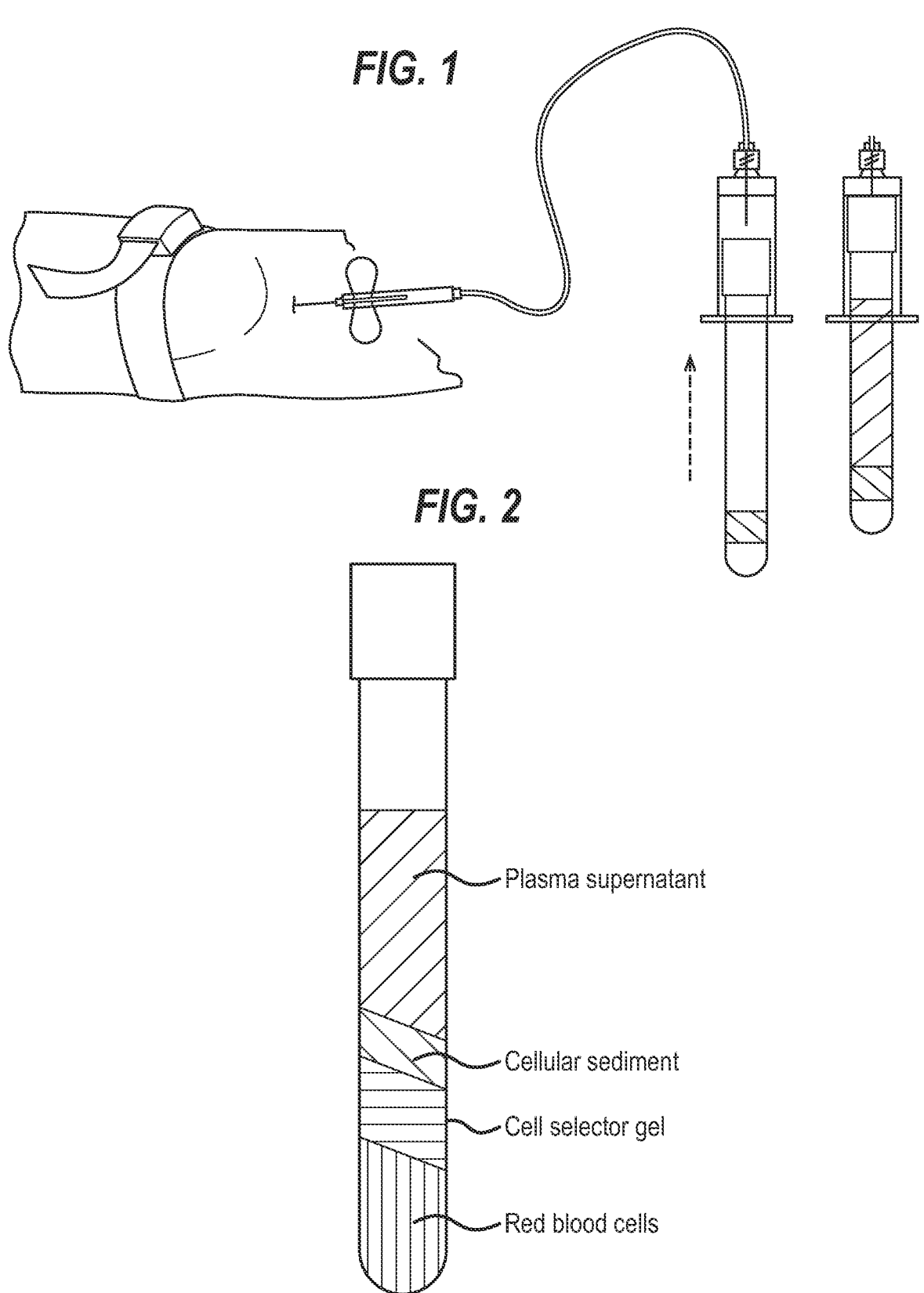
FIG. 1. Schematic view of a tube for the preparation of PRP with blood collection device and accessories.
FIG. 2. Schematic view of a tube for the preparation of PRP displaying the different layers obtained after centrifugation with first the Red Blood Cells (RBCs), followed by the Cell Selector Gel (CSG) or thixotropic gel, then a cellular sediment with finally on top the plasma supernatant containing the Plasma Concentrate (PC) or PRP. A similar tube may be used for the preparation of BMC.

The following paragraphs provide definitions of the terms according to the invention and are intended to apply uniformly throughout the specification and claims unless an otherwise expressly set out definition provides a broader definition.

The expression "thixotropic" means a gel that becomes more fluid as a result of agitation or pressure, i.e. a gel which viscosity is decreasing as a result of agitation or pressure. The term viscosity refers to those characteristics of the specified material(s) determining the degree of gelation, such as for example the firmness or hardness of the material, the degree to which the material resists flowing like a fluid. A thixotropic gel according to the invention comprising a polyester gel or a mixture thereof which is water insoluble and chemically inert to blood constituents which can be used in accordance with the invention. Typical thixotropic gels are used in blood cells separation for diagnostics and proteomics purposes. A thixotropic gel is also herein referred to as a "cell selector gel". Other gels may be used in the present invention. Such gels therefore allow "separation of red blood cells".

The expression "point-of-care" means all services provided to patients at the bedside. All containers, tubes, syringes and/or medical devices according to any aspect or embodiment of the invention may be used point of care.

The expression "phlebotomy accessories" or "venipuncture accessories" means accessories that allow the puncture of a vein with a needle for the purpose of drawing blood. All containers, tubes, syringes and/or medical devices according to any aspect or embodiment of the invention may further comprise phlebotomy accessories or venipuncture accessories.

Alternative expressions for "wound healant" or "wound sealant" or "tissue healant" or "tissue sealant" or "wound healing composition" or "tissue healing composition" are "bioadhesive sealant" or "fibrin glue".

The expression "wound healant" or "wound sealant" or "tissue healant" or "tissue sealant" or "wound healing composition" or "tissue healing composition" or "bioadhesive sealant" or "fibrin glue" means an agent or a composition that is able to promote and/or increase the speed and/or quality of cicatrisation of a wound. Wound healants or sealants are able to promote tissue regeneration. The expression "wound" means any damaged tissue, for example following trauma or surgery. Wounds in mammals, include for examples bed sores, ulcers, lacerations and burns, graft sites (graft donor and acceptor sites), fistulas, periodontal tissue damages, diabetic non-healing wounds, consequences of traumas or any surgery act. In its general sense the expression is intended to also encompass skin damages where the skin surface presents some depression without necessarily a cut on its surface such as age-related tissue damages (e.g. wrinkles) and scars such as for example acne (especially after dermabrasion treatment) or rubella scars.

The expression "PRP" means a platelet-rich-plasma, preferably of mammal origin or human origin, more preferably autologous, prepared by the process of the invention in order to pellet and remove erythrocytes and concentrate the plasma in leucocytes, thrombocytes and adhesion proteins as compared to native whole blood. The expression "autologous" or "autogenic" or "autogenous" means an in-vivo method wherein a single donor's blood, tissue and/or cell is used and wherein the blood, tissue and/or cell extracted from this donor is intended for use on the same donor. A-PRP herein means Autologous Platelet Rich Plasma. As opposed, "allogeneic" methods are using blood, tissue and/or cell from one or more third parties for use on a donor ("homologous" or "heterologous"). An autologous product avoids some of the common problems associated with the use of biological materials from third parties, such as for example screening to assure that the donor was biologically or immunologically compatible with the patient and potential contamination with hepatitis, HIV, prion, Creutzfeld—Jacob's disease and the like. A "plasma concentrate" may refer to a composition containing platelets at a higher concentration than whole blood, like complete plasma or PRP.

The expression "BMC" means a Bone Marrow Concentrate which consists of a concentration of fluid taken from bone marrow. A needle may be used to remove bone marrow from within the bone. This may be done under sedation or general anesthesia. Marrow may be taken from the pelvis but may be taken from other sites. The sample of bone marrow is removed and then spun down in a centrifuge to separate the cells so in order to obtain a liquid herein called BMC that has a high concentration of stem cells. The surgeon may inject the stems cells or BMC directly into the surgical site. Stem cells or BMC may be used to help with bone and joint healing, cartilage repair and new blood vessel growth. Using stem cells or BMC may treat delayed union or nonunion of bone fractures, cartilage defects, osteonecrosis, chronic tendon problems is or chronic wounds.

The expression "coagulation activator" means an agent, for example an enzyme, that is able to trigger or activate coagulation of plasma and platelets aggregation. A coagulation activator comprises a thrombin activator and/or a fibrinogen activator and/or thrombin and/or an autologous thrombin and/or an autologous thrombin serum and/or calcium chloride and/or calcium gluconate and/or calcium saccharate. Coagulation may be combined in order to change the stiffness of compositions.

The expression "thrombin activator" means an agent that is able to activate thrombin and to trigger coagulation. Typical thrombin activators are certain co factors such as sodium or calcium. In practicing this invention, thrombin activation preferably occurs in the presence of calcium ions. Calcium ions are generally added to the platelet concentrate as a salt solution to provide a final concentration generally of or about 0.1 mg/mL of platelet concentrate. Suitable calcium salts include, without limitation, CaCO3, CaSO4 or CaCl2. A preferred calcium salt for use in the invention is calcium gluconate (CaGL). CaGL is available as calcium gel injection, USP 10%. The expression "fibrinogen activator" means an agent that is able to activate the conversion of fibrinogen into fibrin and triggers the formation of the clot. Typical fibrinogen activators are thrombin or batroxobin. The term thrombin may include calcified thrombin, in particular, from or about 100 to about 10 units of thrombin per 1 mL of 10% of aqueous calcium gluconate solution; it may include calcified bovine thrombin, allogeneic thrombin or recombinant human thrombin, preferably autologous thrombin. A fibrinogen activator can be an enriched thrombin composition such as thrombin compositions as described in U.S. Pat. No. 6,472,162 or an autologous thrombin serum according to the invention. A fibrinogen activator may herein be used instead of or in combination with a coagulation activator in any aspect or embodiment of the invention.

The expression "therapeutically effective amount" means the amount or amounts of the constituent elements or combination thereof necessary to enhance wound healing such as, for example, the reduction in the volume or surface area of a wound, the increase in the amount of granulation tissue or other biological material facilitating collagen lay down, vascular in growth, fibroblast proliferation or overall healing; All of the versions of the invention described herein are assumed to have the therapeutically effect amount(s) of constituent substances, or combinations thereof. By the expression "pharmaceutically acceptable carrier" is intended pharmaceutically acceptable additional ingredient such as stabilizers, antimicrobial agents, buffers, adjuvants, anaesthetics, corticosteroids and the like. By the expression "cosmetically acceptable carrier" is intended cosmetically acceptable additional ingredient such as stabilizers, buffers, colouring agents, flavouring agents, adjuvants, and the like.

The expression "Cyclic Olefin Copolymer" (COC) or "Cyclic Olefin Polymer" (COP) means an amorphous polymer, Ethylene Copolymer; COC; COP; Cyclo Olefinecopolymer; Cyclic Olefin Polymer; Ethylene-norbornene Copolymer. COPs use a single type of monomer whereas COCs use different types of monomers. The invention encompasses cyclic olefin copolymers based on different types of cyclic monomers and polymerization methods. The Cyclic olefin copolymers or polymers of the present invention may be produced by chain copolymerization of cyclic monomers such as 8,9,10-trinorborn-2-ene (norbornene) or 1,2,3,4,4a, 5,8,8a-octahydro-1,4:5,8-dimethanonaphthalene with ethene, Ticona's TOPAS, Mitsui Chemical's APEL, or by ring-opening metathesis polymerization of various cyclic monomers followed by hydrogenation (for example Japan Synthetic Rubber's ARTON, Zeon Chemical's Zeonex and Zeonor). All containers, tubes, syringes, accessories of the invention may be made of COC or COP.

The expression "hyaluronic acid" or "HA" (also called hyaluronan or hyaluronate) means an anionic, nonsulfated glycosaminoglycan distributed widely throughout connective, epithelial, and neural tissues. It is unique among glycosaminoglycans in that it is nonsulfated, forms in the plasma membrane instead of the Golgi, and can be very large, with its molecular weight often reaching the million. One of the chief components of the extracellular matrix, hyaluronan contributes significantly to cell proliferation and migration. Hyaluronic acid provides hydration and elasticity of the tissues. Platelet Rich Plasma contains growth factors (PDGF, TGF-ß, IGF, EGF, VEGF) that promote and accelerate healing of hard and soft tissues. When both a biomaterial (e.g. HA) and PRP are applied on damaged tissues, this improves elasticity and accelerates healing.

The expression "chitosan" means a linear polysaccharide composed of randomly distributed β-(1-4)-linked D-glucosamine (deacetylated unit) and N-acetyl-D-glucosamine (acetylated unit). Chitosan is produced commercially by deacetylation of chitin , which is the structural element in the exoskeleton of crustaceans (crabs, shrimp, etc.) and cell walls of fungi. The degree of deacetylation (% DD) can be determined by NMR spectroscopy, and the % DD in commercial chitosans is in the range 60-100%. On average, the molecular weight of commercially produced chitosan is between 3800 to 20,000 daltons. A common method for the synthesis of chitosan is the deacetylation of chitin using sodium hydroxide in excess as a reagent and water as a solvent. This reaction pathway, when allowed to go to completion (complete deacetylation) yields up to 98% product. The amino group in chitosan has a pKa value of ~6.5, which leads to a protonation in acidic to neutral solution with a charge density dependent on pH and the % DA-value. This makes chitosan water soluble and a bioadhesive which readily binds to negatively charged surfaces such as mucosal membranes. Chitosan enhances the transport of polar drugs across epithelial surfaces, and is biocompatible and biodegradable.

A blood, bone marrow, cells and/or platelet preservation and/or stimulating solution may herein be defined as a solution that is able to preserve the shape, function and/or efficiency or blood or bone marrow constituents and/or able to activate, stimulate or enhance activity, efficiency, function of blood or bone marrow constituents, enhance, stimulate or activate release of growth factors or other factors present in blood or bone marrow constituents, of cells and/or platelets, to stimulate cell or platelet proliferation.

BCT herein stands for Blood Cell Therapy(ies) or Blood Collection Tube(s).

The present invention relates to new methods and medical devices enabling the preparation of Platelet Concentrates (PC) or Bone Marrow Concentrates (BMC) alone or in combination with biomaterials such as hyaluronic acid, preferably in large volumes.

Advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

The invention relates to sterile and non-pyrogenic containers, preferably tubes allowing the mix of a PC (for example Platelet Rich Plasma (PRP)) or BMC, with biomaterials, for example Hyaluronic Acid (HA) advantageously in the same proportion (e.g. 4 mL of PRP for 4 mL of HA), advantageously optionally in large volumes. In one embodiment, the invention relates to a medical device consisting of or comprising one tube for the preparation of PC or BMC and one tube prefilled with hyaluronic acid preferably connected through means of a device enabling transfer of PC or BMC into the tube prefilled with the biomaterial. Preferably such transfer occurs automatically, for example due to vacuum in the tube containing the biomaterial. The aspects and embodiments of the present invention enable the preparation of a combination of a Platelet Concentrate (PC) or Bone Marrow Concentrate (BMC) with a biomaterial or cell extract at a volume of at the least 3 ml, 4 ml, 5 ml, 6 ml, 7 ml, 8 ml, 9 ml, 10 ml or more.

The PC/BMC tube (tube allowing the preparation of PC and/or BMC) may allow the preparation of 4 mL of PRP/BMC and may contain an inert polyester cell-selector gel and a liquid anticoagulant. The HA tube is dedicated to the direct transfer of PRP/BMC from the PRP/BMC tube and its mix with Hyaluronic Acid. The HA tube may contain only a gel of hyaluronic acid, at about 4 mL. Both tubes are preferably for single use only and are designed to be used with sterile and single-use phlebotomy material provided in the same kit.

In a first aspect, the invention provides a container (FIG. 1, FIG. 2, FIG. 3 upper part, FIG. 4 upper part) for the preparation of Bone Marrow Concentrate (BMC) and/or Plasma Concentrate (PC), characterized in that:

a) said container comprises or is prefilled with:
  i) at the least one anticoagulant, and/or
  ii) at the least one filter and/or composition allowing separation of red blood cells (RBCs), preferably or optionally a cell selector gel (CSG), preferably or optionally a thixotropic gel, preferably or optionally an inert polyester CSG, and
  iii) optionally at the least one biomaterial preferably or optionally selected from hyaluronic acid, chitosan, silk protein or fibroin or any combination thereof, and
  iv) optionally at the least one blood, bone marrow, cells and/or platelet preservation and/or stimulating solution, preferably or optionally plasmalyte-A, and
b) optionally a collection device, optionally or preferably comprising or consisting of a collection holder with accessories, preferably or optionally a safety lock and butterfly needle (FIG. 1), may be affixed to said container for collection of blood and/or bone marrow into said container and wherein said collection preferably or optionally occurs in closed circuit, preferably or optionally automatically, preferably or optionally by vacuum, and
c) optionally a collection device may be affixed to said container for collection of thrombin serum, preferably or optionally autologous thrombin serum, into said container and wherein said collection preferably or optionally occurs in closed circuit, preferably or optionally automatically, and
d) optionally a transfer device (FIG. 3, FIG. 4) can be affixed to said container for the transfer of said PC and/or said BMC into another container, wherein said container is preferably or optionally a tube or syringe, preferably or optionally under vacuum, wherein said transfer preferably or optionally occurs in closed circuit, preferably or optionally automatically, preferably or optionally by vacuum, preferably or optionally either by direct contact between the two containers or through means of a device, and
e) optionally further comprises at least one filter or substance for the separation of other blood components and/or bone marrow components, optionally or preferably for lymphocytes,
f) said container optionally is under vacuum, and may be suitable:
  i) for collection of bone marrow and/or whole blood into said container, and
  ii) for centrifugation, and

iii) optionally for vacuum and/or mixing and/or inversion of said container, and may be suitable for either or both:
  iv) collection of said PC and/or BMC from said container, and/or
  v) transfer of said PC and/or BMC into another container.
  "Suitable for" may herein (in any aspect or embodiment of the invention) be substituted by "when used in".

In accordance with this aspect of the invention, the container may contain either:
  i) at least one anticoagulant, or
  ii) at the least one filter and/or composition allowing separation of red blood cells (RBCs), preferably or optionally a cell selector gel (CSG), or
  iii) a combination of at least one anticoagulant and:
    a. at the least one filter, or
    b. composition allowing separation of red blood cells (RBCs), preferably or optionally a cell selector gel (CSG), or
    c. a combination of at the least one filter and a composition allowing separation of red blood cells (RBCs), preferably or optionally a cell selector gel (CSG).

In a second aspect, the invention provides a container (FIG. 3, lower part) for the preparation of PC and/or BMC in combination with at the least one biomaterial preferably or optionally selected from hyaluronic acid, chitosan, silk protein or fibroin, cell extract or any combination thereof, characterized in that:

a) said container (FIG. 3, lower part) comprises or is prefilled with a biomaterial preferably or optionally selected from hyaluronic acid, chitosan, silk protein or fibroin, cell extract or any combination thereof, and
b) optionally a collection device (FIG. 3), preferably or optionally comprising a collection holder, may be affixed to said container for the collection of PC and/or BMC into said container, and
c) optionally said PC and/or BMC in combination with at the least one biomaterial can be collected, preferably or optionally in closed circuit, and
d) said container optionally further comprises or is prefilled with a coagulation activator, preferably or optionally selected from thrombin serum, calcium gluconate and/or calcium chloride, and
e) said container optionally is under vacuum,
f) said container optionally contains two or more chambers wherein each chamber may contain a composition selected from a substance, biomaterial, cell extract, PC or BMC and/or coagulation activator, wherein said compositions are isolated from each other in their respective chamber and wherein said compositions may optionally enter into contact with each other or be mixed together inside and or outside said container, wherein said chambers are separated by a chemical or biological substance, membrane or any other means of separation, wherein such means of separation may optionally disintegrate over time or is biodegradable, and may be suitable for:
  i) collection of PC and/or BMC from a PC and/or BMC container, preferably or optionally from the container of the first aspect, wherein said transfer optionally occurs in closed circuit, preferably or optionally automatically, preferably or optionally by vacuum, preferably or optionally either by direct contact between the two containers or through means of a collection device, and
  ii) optionally centrifugation, and iii) collection or transfer of said PC and/or BMC in combination with at the least one biomaterial into another device, preferably or optionally syringe, preferably or optionally in closed circuit, preferably or optionally automatically, and iv) optionally mixing and/or inversion.

In a third aspect, the invention provides a syringe (FIG. 4, lower part) for the preparation of PC and/or BMC in combination with at the least one biomaterial preferably or optionally selected from hyaluronic acid, chitosan, silk protein or fibroin, cell extract or any combination thereof, characterized in that:

a) said syringe (FIG. 4, lower part) comprises or is prefilled with a biomaterial preferably or optionally selected from hyaluronic acid, chitosan, silk protein or fibroin, cell extract or any combination thereof, b) optionally a collection device (FIG. 4), preferably or optionally a collection holder, can be affixed to said syringe for the collection of PC and/or BMC into said syringe, c) optionally said syringe comprises or is prefilled with a coagulation activator, preferably or optionally selected from thrombin serum, calcium gluconate and/or calcium chloride, d) said syringe optionally contains two or more chambers wherein each chamber may contain a composition selected from a substance, biomaterial, cell extract, PC or BMC and/or coagulation activator, wherein said compositions are isolated from each other in their respective chamber and wherein said compositions may optionally enter into contact with each other or be mixed together inside and or outside said syringe, wherein said chambers are separated by a chemical or biological substance, membrane or any other means of separation, wherein such means of separation may optionally disintegrate over time or is biodegradable, and may be suitable for:

i) collection of PC and/or BMC from a PC and/or BMC container, preferably or optionally from the container of the first aspect of the invention, wherein said collection preferably or optionally occurs in closed circuit, either by direct contact between said syringe and said container or through means of a collection device, preferably or optionally automatically, and ii) optionally inversion, and iii) optionally application or injection of said PC and/or BMC in combination with at the least one biomaterial on or into a human or animal, preferably or optionally in closed circuit, preferably or optionally automatically.

In further embodiments, the invention provides a container or syringe according to any of the previous aspects further prefilled with or comprising:

i) at the least one anticoagulant, and/or ii) at the least one filter and/or composition allowing separation of red blood cells (RBCs), preferably or optionally a cell selector gel (CSG), preferably or optionally a thixotropic gel, preferably or optionally an inert polyester CSG, and/or iii) optionally at the least one biomaterial preferably or optionally selected from hyaluronic acid, chitosan, silk protein or fibroin or any combination thereof, and/or iv) optionally at the least one PC or BMC preservation solution, optionally or preferably plasmalyte-A, and/or v) optionally at the least one coagulation activator, thrombin serum, tricalcium phosphate (TCP), a bone substitute, hyaluronic acid composition, calcium gluconate, calcium saccharate, chitosan, fibroin, fibroin-silk protein or fibroin proteins, growth factors, mannitol, collagen, albumin, ascorbic acid, cream, fat cells, fat tissue, bone marrow concentrate, lubricin, cd-gelatin, botulinum toxin and/or one or more cell extracts, preferably an autologous cell extract, selected from an extract of keratinocytes, bone marrow, fibroblasts, periosteum or corneal cells, melanocytes and Langerhans cells, fat cells, muscle cells such as myoblasts and satellite cells, osteoblasts, chondrocytes, umbilical cord cells, stem cells, mesenchymal stem cells (MSCs), preadipocytes, adipocytes, pre-endhotelial cells, Schwann cells or Achilles tendon cells.

In further embodiments, the invention provides the container or syringe according to any of the previous aspects or embodiments further characterized in that:

a) at the least two containers, at the least one container and one syringe or at the least two syringes may be connected together through means of a connecting device enabling transfer of any substance, material, PC, BMC, cell extract or composition from one container or syringe to the other container or syringe, b) said container is a tube, and/or c) said tube or syringe allows the withdrawal of about 1 ml to about 20 ml of whole blood, bone marrow, PC or BMC, preferably or optionally about 2 ml to about 10 ml, preferably or optionally about 4 ml.

d) said container and/or syringe is sterile and/or non-pyrogenic, and/or e) said container is suitable for the preparation of PRP, autologous PRP, PC, autologous PC and/or autologous BMC, and/or f) said container is suitable for the preparation of about 2 ml to about 10 ml, preferably or optionally about 3 ml to about 6 ml, preferably or optionally about 4 ml of PRP, autologous PRP, autologous PC and/or autologous BMC, and/or g) said syringe is prefilled with or comprises from about 0.5 ml to about 5 ml of biomaterial, preferably or optionally about 2 ml of biomaterial, and/or h) said container is prefilled with or comprises from about 1 ml to about 4 ml of cell-selector gel, preferably or optionally from about 1.5 ml to about 3.5 ml, preferably or optionally about 1.5 ml, about 2 ml, about 2.5 ml or about 3 ml of cell-selector gel, and/or i) said container comprises or is prefilled with about 0.2 ml to about 1 ml of anticoagulant, preferably or optionally about 0.6 ml of anticoagulant, preferably or optionally sodium citrate, from about 2% to about 6%, preferably or optionally about 4%, and/or j) said container or syringe contains from about 1 ml to about 5 ml of hyaluronic acid, preferably or optionally about 2 ml of hyaluronic acid, and/or k) said hyaluronic acid is in the form of a gel, and/or l) said hyaluronic acid resides in a buffer, preferably or optionally phosphate buffer, preferably or optionally comprising or consisting of sodium chloride, dipotassium hydrogenphosphate, potassium dihydrogenphospate, potassium chloride and water, and/or m) said hyaluronic acid is suitable for injection, mesotherapy, and/or application, and/or n) said hyaluronic acid is present from about 40 mg to about 200 mg per container, preferably or optionally about 80 mg per container, and/or o) said hyaluronic acid has a molecular weight of about 1000 KDa to about 2000 KDa, preferably or optionally about 1550 KDa, and/or p) said hyaluronic acid is at about 0.1% to about 3%, preferably about 1% to about 2%, and/or q) said hyaluronic acid is obtained by fermentation, and/or r) said container is prefilled:
   1. during the manufacturing process and/or
   2. before centrifugation, either before and/or after collection of blood or bone marrow into said container, and/or
   3. with at the least one substance, biomaterial, gel and/or anticoagulant or any combination thereof and is contained in a kit or medical device.

In a fourth aspect, the invention provides a medical device or kit consisting of or comprising either:

a) at the least one container and/or at the least one syringe according to any of the aspects or embodiments.

b) at the least one container of the first aspect of the invention, at the least one container of the second aspect of the invention and/or at the least one syringe of the third aspect of the invention or any combination thereof, c) at the least one container of the first aspect of the invention and at the least one container of the second aspect of the invention, d) at the least one container of the first aspect of the invention and at the least one syringe of the third aspect of the invention, e) at the least one container of the first aspect of the invention, at the least one container of the second aspect of the invention and at the least one syringe of the third aspect of the invention, f) at the least one container of the second aspect of the invention and at the least one syringe of the third aspect of the invention, g) at the least one container of the first aspect of the invention for the preparation of PC and at the least one container of the first aspect of the invention for the preparation of BMC, h) at the least one container of the first aspect of the invention for the preparation of PC and/or at the least one container of the first aspect of the invention for the preparation of BMC, and at the least one container of the second aspect of the invention comprising or prefilled with a cell extract and at the least one container of the second aspect of the invention comprising or prefilled with hyaluronic acid, chitosan, silk protein or fibroin or any combination thereof, i) at the least one container of the first aspect of the invention for the preparation of PC and/or at the least one container of the first aspect of the invention for the preparation of BMC, and at the least one container of the second aspect of the invention comprising or prefilled with a cell extract and at the least one syringe of the third aspect of the invention comprising or prefilled with hyaluronic acid, chitosan, silk protein or fibroin or any combination thereof, j) at the least one container of the first aspect of the invention for the preparation of PC and/or at the least one container of the first aspect of the invention for the preparation of BMC, and at the least one syringe of the third aspect of the invention comprising or prefilled with a cell extract and at the least one container of the second aspect of the invention comprising or prefilled with hyaluronic acid, chitosan, silk protein or fibroin or any combination thereof,
wherein said medical device or kit optionally further comprises:

k) a the least one container of the first aspect of the invention, a container of the second aspect of the invention and/or a syringe of the third aspect of the invention or any combination thereof, and/or l) a the least one container for the preparation of thrombin serum, preferably autologous thrombin serum, and/or m) a connecting device enabling transfer of any substance, material, PC, BMC, cell extract or composition from one container or syringe to another container or syringe.

In further embodiments, the invention provides a medical device or kit comprising:

a) the container according to the first aspect of the invention, and b) the container of the first aspect of the invention, the container of the second aspect of the invention or the syringe of the third aspect of the invention, and c) optionally a collection device for collecting blood or bone marrow preferably or optionally comprising or consisting of a collection holder with preferably or optionally a safety lock and butterfly needle, and d) optionally a collection device preferably or optionally comprising or consisting of a collection holder and transfer device for collecting PC and/or BMC into said container of the first aspect of the invention, said container of the second aspect of the invention and/or said syringe of the third aspect of the invention, and e) optionally accessories and/or single use phlebotomy material.

In further embodiments, the invention provides a medical device or kit comprising:

a) a tube for the preparation of PRP or BMC under vacuum allowing the withdrawal of about 4 mL of blood or bone marrow which contains:
   ii. about 2.5 mL of inert cell-selector gel
   iii. about 0.6 mL of anticoagulant, preferably or optionally sodium citrate at about 4%, b) a tube under vacuum allowing the withdrawal of about 4 mL of PRP or BMC from said tube a), which contains about 2 mL of hyaluronic acid gel in phosphate buffer, preferably or optionally sodium chloride, dipotassium hydrogenphosphate, potassium dihydrogenphospate, potassium chloride and water for injection, c) a collection device for collecting blood and/or bone marrow consisting of a collection holder with a safety lock and butterfly needle, d) a collection device preferably or optionally consisting of a collection holder and transfer device for collecting PC and/or BMC from said tube a) into said tube b).

In further embodiments, the invention provides a medical device or kit comprising:

a) a tube for the preparation of PRP or BMC under vacuum allowing the withdrawal of about 4 mL of blood or bone marrow which contains:
   i. about 2.5 mL of inert cell-selector gel
   ii. about 0.6 mL of anticoagulant, preferably or optionally sodium citrate at about 4%, b) a syringe allowing the withdrawal of about 4 mL of PRP or BMC from said tube a), which contains about 2 mL of hyaluronic acid gel in phosphate buffer, preferably or optionally sodium chloride, dipotassium hydrogenphosphate, potassium dihydrogenphospate, potassium chloride and water for injection, c) a collection device for collecting blood and/or bone marrow consisting of a collection holder with a safety lock and butterfly needle, d) a collection device preferably or optionally consisting of a collection holder and transfer device for collecting PC and/or BMC from said tube a) into said syringe b).

In further embodiments, the invention provides a medical device or kit according to any of the previous aspects or embodiments, further comprising a tissue harvesting cannula, preferably or optionally a fat-tissue harvesting cannula, a cannula for injection preferably or optionally straight or concave, a piston stopper, at the least one self-adhesive disc, a luer connector, anesthetic solution, injection accessories such as needles and/or syringes, syringes for tissue harvesting and mixing preferably or optionally luer-lock syringes, at the least one transfer cannula, a clip device, a container with dispenser for dispensing PC and/or BMC, a trocar, ampoule of coagulation activator such as calcium chloride or calcium gluconate, a paper mask, a is device for the simultaneous release of PC and thrombin serum or any other combination of PC, BMC, substance, biomaterial or coagulation activator, wherein such device comprises at least one syringe, a noozle for spray application, a double piston stopper, an applicator syringe holder and/or a connector, or any combination thereof.

In a fifth aspect, the invention provides a method for the preparation of a composition, preferably PC and/or BMC optionally in combination with at the least one biomaterial preferably or optionally selected from hyaluronic acid, chitosan, silk protein or fibroin or any combination thereof using at least one, two, three, four, five, six, seven, eight, nine, ten or more container(s) and/or syringe(s) according to any of the previous aspects or embodiments, wherein the method is preferably or optionally for use in therapy, dermatology, dentistry, orthopedics, sports medicine, cosmetics, esthetics, surgery, ophthalmology, mesotherapy, injections, infiltrations, subcutaneous applications, wound care, volume enhancement, volume corrections, mechanical support and/or visco-supplementation.

In a sixth aspect, the invention provides a composition, preferably PC and/or BMC optionally in combination with at the least one biomaterial preferably selected from hyaluronic acid, chitosan, silk protein or fibroin or any combination thereof, obtained using at least one, two, three, four, five, six, seven, eight, nine, ten or more container(s) and/or syringe(s) according to any of the previous aspects or embodiments or obtained by using a method according to any of the previous aspects or embodiments, said composition optionally further combined with a coagulation activator, thrombin serum, tricalcium phosphate (TCP), a bone substitute, hyaluronic acid composition, calcium gluconate, calcium saccharate, chitosan, fibroin, fibroin-silk protein or fibroin proteins, growth factors, mannitol, collagen, albumin, ascorbic acid, cream, fat cells, fat tissue, bone marrow concentrate, lubricin, cd-gelatin, botulinum toxin and/or one or more cell extracts, optionally or preferably an autologous cell extract, selected from an extract of keratinocytes, bone marrow, fibroblasts, periosteum or corneal cells, melanocytes and Langerhans cell, fat cells, muscle cells such as myoblasts and satellite cells, osteoblasts, chondrocytes, umbilical cord cells, stem cells, mesenchymal stem cells (MSCs), preadipocytes, pre-endhotelial cells, Schwann cells or Achilles tendon cells, wherein said composition is preferably or optionally for use in therapy, dermatology, dentistry, orthopedics, sports medicine, cosmetics, esthetics, surgery, ophthalmology, ss mesotherapy, injections, infiltrations, subcutaneous applications, wound care, volume enhancement, volume corrections, mechanical support and/or visco-supplementation.

In another aspect, the invention provides a method of treatment for healing of wounds or tissues or for promoting bone or periodontum growth and/or bone and/or tissue regeneration such as skin, cartilage, muscle, tendon, ligament, adipose tissue, cornea, peripheral nerves, spine or bone using at least one, two, three, four, five, six, seven, eight, nine, ten or more container(s) and/or syringe(s) according to any of the previous aspects or embodiments.

In a seventh aspect, the invention provides for the use of a composition, method, medical device, kit, container or syringe according to any of the previous aspects or embodiments in therapy, dermatology, dentistry, orthopedics, sports medicine, cosmetics, esthetics, surgery, ophthalmology, mesotherapy, injections, infiltrations, subcutaneous applications, wound care, volume enhancement, volume corrections, mechanical support and/or visco-supplementation, on/for a wound, a damaged tissue, damaged bone or periodontal defect or cavity, for cellular regeneration, for tissue adhesion, for promoting wound healing or tissue healing and/or sealing and/or regeneration of a tissue and/or a cartilage and/or a bone and/or a nerve in a wound or tissue of a human or animal, or for inducing periodontal regeneration in a wound or a periodontal defect of a mammal with periodontal disease or other condition requiring periodontal regeneration, or for ligament and/or cartilage reconstitution, or for promoting skin regeneration in a scar or a wrinkle, or for increasing adipose tissue volume in a mammal with a dermal fat graft or other condition requiring adipose tissue regeneration, or for inducing myocardial regeneration in a mammal with myocardial deficiency or other condition requiring myocardial regeneration tissue regeneration, or for inducing corneal regeneration in a mammal with corneal deficiency or other condition requiring corneal regeneration, or for inducing articular or cartilage regeneration in a mammal with articular or cartilage deficiency or other condition requiring articular or cartilage tissue regeneration, or for promoting skin regeneration in a scar, a wrinkle or a fat deficiency from human or lower animal, or for inducing peripheral nerve regeneration in a mammal with peripheral nerve damage, nerve suture or spinal cord injury or other condition requiring peripheral nerve regeneration, or for inducing bone regeneration in a mammal with bone damage, bone deficiency or other condition requiring bone regeneration, or for injections for orthopedic and injections for esthetic, or for regeneration and/or rejuvenation of skin tissues, particularly in promoting and/or initiating skin regeneration such as reducing skin wrinkles, deep wrinkles, acne, burns, rubella or small pox scars, vitiligo and lipoatrophy, amelioration of nasolabial lines and treatment of skin damages or disorders such as skin burns, Kaposi's sarcoma, skin skeloids or Dupuytren's palmar fibromatosis and in the reduction of pain associated with skin and tissue regeneration, or for wound or tissue healing or regeneration treatments, especially the treatment of traumatic or surgical wounds such in the fitting and/or holding and/or sealing of native or prosthetic grafts; treatment of vasculitis; ulcers such as diabetic neuropathic ulcers or decubitus sores, diabetic ulcer, perforating ulcer or diabetic perforating ulcer, arthritis, osteoarthritis, pseudo-arthritis, radiodermatitis and closing fistulas, fistulas or for cardiac disorders, cardiac regeneration such as in the treatment of heart failure, chronic cardiac failure, ischemic and non-ischemic cardiac failure and cardiomyopathy, or for bone, cartilage and articular disorders such as chondral damage, cartilage and/or bone injury such as deep cartilage damage and/or erosion and/or arthroscopy, tendon torn and rotator cuff in shoulder, or for corneal disorders such as dry eye syndrome; corneal opacity such as those caused by chemical burns, affliction by Steven's Johnson syndrome; scarring of the cornea and corneal ulcers, or for peripheral nerve damage, nerve suture and spinal cord injury, diabetic wounds, large vascular wounds, deep injections, intra dermal injections, intra-articular infiltrations, ophthalmic collyre, eyewash, for articulations, muscular lesions, as a mask post laser, post peeling, monotherapy, for glitter, gloss, brilliance or brightness.

In one embodiment, the invention relates to a medical device comprising or consisting of:
- a. a safety—Lock Butterfly needle assembled with collection holder,
- b. a preassembled transfer device
- c. a tube under vacuum allowing the withdrawal of blood, which contains:
  - i) about 2.5 mL of inert cell-selector gel,
  - ii) about 0.6 mL of anticoagulant (e.g., sodium citrate 4%),
- d. a tube under vacuum allowing the withdrawal of PRP, which contains about 2 mL of hyaluronic acid gel in phosphate buffer (Sodium chloride, Dipotassium hydrogenphosphate, Potassium dihydrogenphosphate, Potassium chloride and water for injection), with Hyaluronic Acid preferably at about 80 mg per tube, at about 1550 KDa and preferably obtained from fermentation.

The containers and syringes of the present invention may be applied on large or deep wounds, or as biological glue.

The containers and syringes of the present invention containing a biomaterial are preferably sterilized by moist steam and preferably packaged under low germ atmosphere. Other containers, syringes or components of the present invention, e.g., tubes for the preparation of PC, basic phlebotomy material are preferably sterilized by exposure to a minimum dose of about 25 kGy gamma irradiation after preferably double blister packaging.

In order to obtain the most efficient effect and a longer pain reduction, it is recommended to apply one dose of biomaterial with either PRP or PC, e.g., about 8 mL of HA/PRP mix, per treatment. The treatment may be either unique in case of surgery, or repeated each week in case of deep wounds, according to the physician decision. Several areas may be treated at the same time.

In another aspect, the invention provides a method for the preparation of a biomaterial in combination with PC or BMC comprising the steps of:
- i) Collecting whole blood in at the least one container or syringe according to any of the previous aspects or embodiments, preferably by
  - a. performing a venous puncture preferably using a butterfly needle connected to a collection holder,
  - b. optionally piercing the stopper of a container to fill it with the whole blood using an internal needle of a collection system. Preferably, a vacuum within the container will enable automatic collection of the necessary volume of blood, e.g., about 8 ml,
  - c. optionally carefully turning the container upside down preferably several times,
  - d. optionally closing the blood collection needle preferably with a safety-Lock system,
- ii) Centrifuging, preferably during about 5 minutes to about 10 minutes, preferably at a centrifugal force of about 1500 g,
- iii) Optionally homogenizing of PC or BMC, preferably by gently inverting the container several times, preferably re-suspending the cellular deposit in the supernatant (about 4 ml of PC or BMC may be obtained),

- iv) Optionally transferring of PC or BMC in a container or syringe containing a biomaterial and/or cell extract, preferably by:
  - a. Connecting the PC or BMC container on a transfer device,
  - b. Reversing the PC or BMC container in order to have the PC or BMC in contact with the stopper of the container,
  - c. Connecting the container or syringe containing the biomaterial and/or cell extract on the transfer device,
  - d. Waiting until PC or BMC is completely transferred in the container or syringe containing the biomaterial and/or cell extract,
  - e. Disconnecting the container or syringe containing the biomaterial and/or cell extract from the transfer device.
- v) Optionally homogenizing the resulting mix PC/BMC with biomaterial/cell extract, preferably by gently inverting the container or syringe several times, preferably by homogenizing of the mix PC/BMC with biomaterial/cell extract (about 8 ml of mix may be obtained),
- vi) Optionally applying, preferably by harvesting, the PC/BMC with biomaterial/cell extract, preferably in a syringe (partial or entire dose to be applied).

In further aspects, the invention provides a fat harvesting cannula, a multiple connector device allowing mixing of different substances or compositions, a medical device comprising such cannula and/or multiple connector device, methods using such devices for fat harvesting, fat washing, fat enrichment and uses thereof. Advantageously, these methods involve fewer and easier steps (less time consuming and more economical) than conventional methods, entirely performed in closed circuit. Advantageously, the methods involve a single procedure (all steps may be performed without required interruption), point of care by the physician or surgeon.

Figure 9:
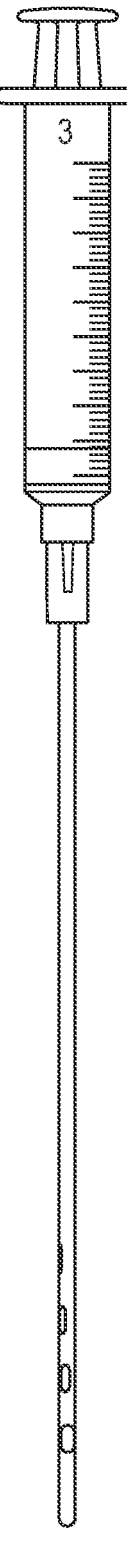
FIG. 9. Schematic view of a cannula (fat harvesting cannula) connected to a syringe (in order to collect the fat tissue harvested by the cannula). Such syringe of FIG. 9 may be connected for example to the multiple connector device of FIG. 8.

In another aspect, the invention provides a method for the preparation of adipocytes in combination with PC comprising the steps of:
- i) Preparing an adipose extract, preferably by
  - a. connecting a harvesting cannula (e.g. as shown in FIGS. 9 and 10) to a syringe (e.g. a 10 ml Luer-Lok), incising the insertion site of the cannula, and harvesting adipose tissue,
  - b. optionally purifying adipose tissue preferably by washing, sedimentation and/or centrifugation
- ii) simultaneously or sequentially of step i) collecting whole blood in a container or syringe according to the invention preferably by:
  - a. Performing a venous puncture preferably using a butterfly needle connected to a collection holder,
  - b. Optionally piercing the stopper of the container to fill it with the whole blood using preferably an internal needle of a collection system. Preferably, a vacuum within the container will enable automatic collection of the necessary volume of blood, e.g. about 8 ml. Preferably a self-adhesive disc is used to plug the hole in the protective film covering the container.
  - c. Optionally carefully turning the tubes upside down several times,
  - d. Optionally closing the blood collection needle preferably with a safety-Lock system,
- iii) Centrifuging, preferably during about 5 minutes to about 10 minutes, preferably at a centrifugal force of about 1500 g, iv) Optionally homogenizing of PC, preferably by gently inverting the container several times, preferably resuspending the cellular deposit in the supernatant (about 4 ml of PC may be obtained), v) preparing and combining adipocytes with PC by preferably:

a. connecting a transfer device to a syringe (e.g. 10 ml) containing purified adipose tissue, b. introducing the PC container in the transfer device, c. collecting the desired volume of PC, d. connecting preferably a Luer connector to the syringe and then preferably a second syringe to the other side of the Luer connector, e. transferring the content from one syringe to the other to mix PC and purified fat tissue, preferably using a cannula (straight or concave) to inject the mixture.

In another aspect, the invention provides a method for the preparation of a composition containing stem cells comprising the steps of:

i) Collecting biological tissue, preferably fat tissue, or biological fluid, preferably Bone Marrow, and ii) Processing said biological tissue, preferably adipose tissue, or said biological fluid, preferably bone marrow, until obtaining suitable tissue/cells (e.g. adipocytes or tissue with desired stem cells) or bone marrow concentrate (BMC), and iii) Either:

a. Enriching or mixing said tissue cells, adipocytes or said BMC with either a biomaterial, PC, PRP, PC combined with hyaluronic acid, hyaluronic acid, PC combined with chitosan, PC combined with silk, chitosan or silk, or b. Culturing said adipose tissue of steps i), ii), iv) or v) into either 20-80% PC, PRP, biomaterial, PC combined with hyaluronic acid, hyaluronic acid, PC combined with chitosan, PC combined with silk, chitosan or silk, and iv) Optionally injecting resulting composition containing stem cells from step iii-a) or iii-b) preferably percutaneously or applying on desired site.

In another aspect, the invention provides a method for the preparation of adipocytes in combination with PC comprising the steps of:

i) Collecting adipose tissue with a cannula, for example with a cannula as shown in FIGS. 9 and 10 and with a syringe connected in closed circuit to such cannula as shown in FIG. 9, and ii) Aspirating adipose tissue through cannula into syringe in a simultaneous or sequential manner to step i); in another embodiment the adipose tissue is transferred from cannula to syringe by another means than aspiration, and iii) Optionally connecting said syringe with a connector to another syringe, iv) Optionally mixing of said adipose tissue preferably by back and forth movements until bursting of adult adipocytes or during 15 seconds, 30 seconds, 1 minute, 2 minutes, 3 minutes, 4 minutes or 5 minutes, and v) Optionally washing adipose tissue with a washing solution, preferably Phosphate-Buffered Saline (PBS) or physiological serum solution, preferably until elimination of triglycerides or formation of a "clean" adipose tissue, or during 15 seconds, 30 seconds, 1 minute, 2 minutes, 3 minutes, 4 minutes or 5 minutes, preferably 30 seconds, and vi) Either:

a. Enriching (e.g. 20 seconds, 30 seconds, 40 seconds, 1 minute, 2 minutes, preferably 30 seconds) or mixing said adipose tissue with a biomaterial, PC, PRP, PC combined with hyaluronic acid, hyaluronic acid, PC combined with chitosan, PC combined with silk, chitosan or silk, or b. Culturing said adipose tissue of steps i), ii), iv) or v) into 20-80% PC, PRP, biomaterial, PC combined with hyaluronic acid, hyaluronic acid, PC combined with chitosan, PC combined with silk, chitosan or silk, and vii) Optionally injecting resulting composition preferably percutaneously or applying on desired site.

The step of mixing of said adipose tissue preferably by back and forth movements until bursting of adult adipocytes enables collection of a matrix, of stem cells nests, and/or of pericytes.

Figures 3, 4:
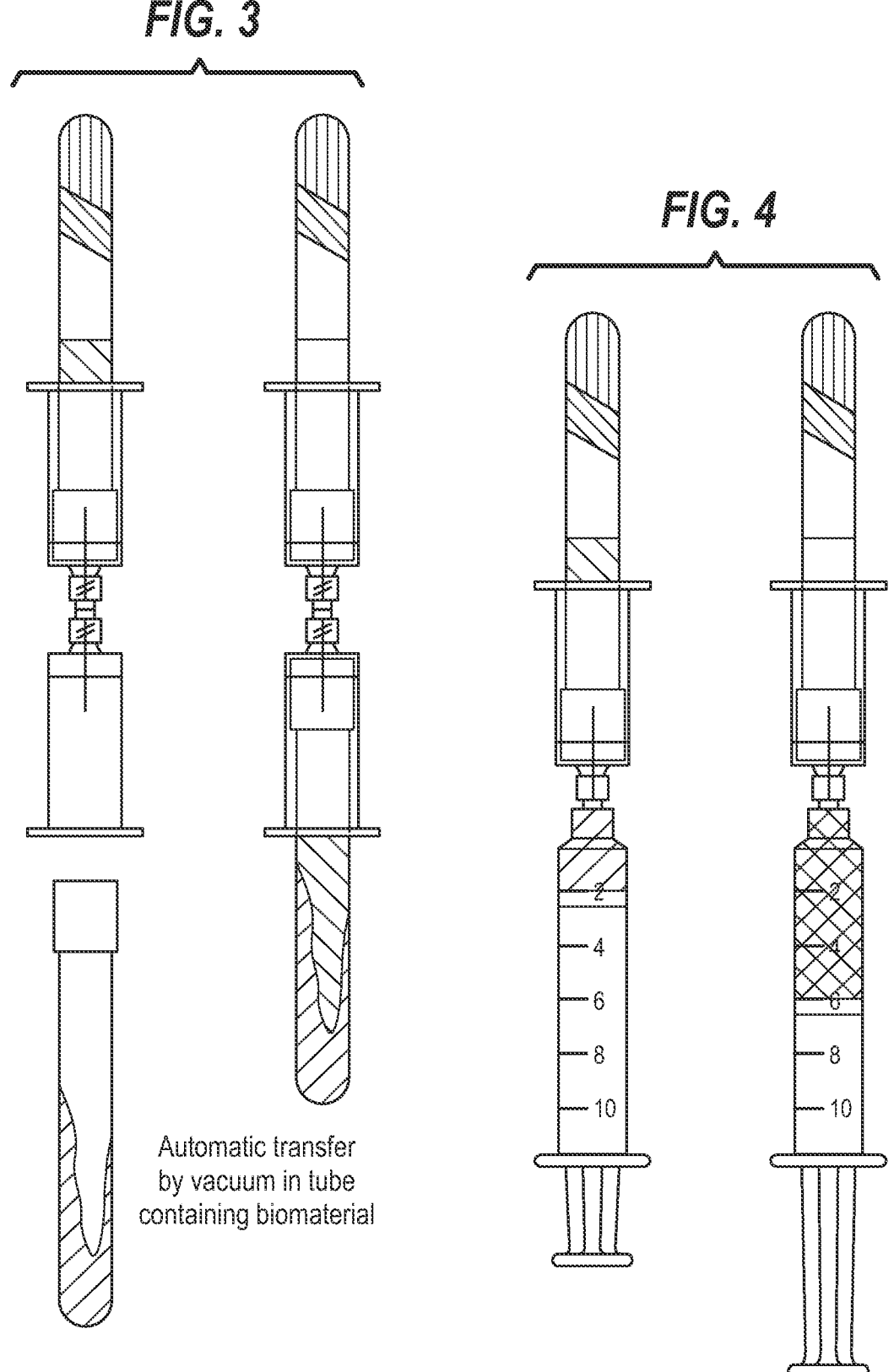
FIG. 3. Schematic view of a first tube for the preparation of PRP and of a second tube comprising or prefilled with a biomaterial (e.g., in the Figure hyaluronic acid) with a device for transferring the PRP of the first tube into the second tube in order to obtain a composition comprising PRP and a biomaterial. Such transfer may occur automatically with second tube under vacuum.
FIG. 4. Schematic view of a tube for the preparation of PRP and of a syringe comprising or prefilled with a biomaterial (e.g., in the Figure hyaluronic acid) with a device for transferring the PRP of the tube into the syringe in order to obtain a composition comprising PRP and a biomaterial.
Figure 5:
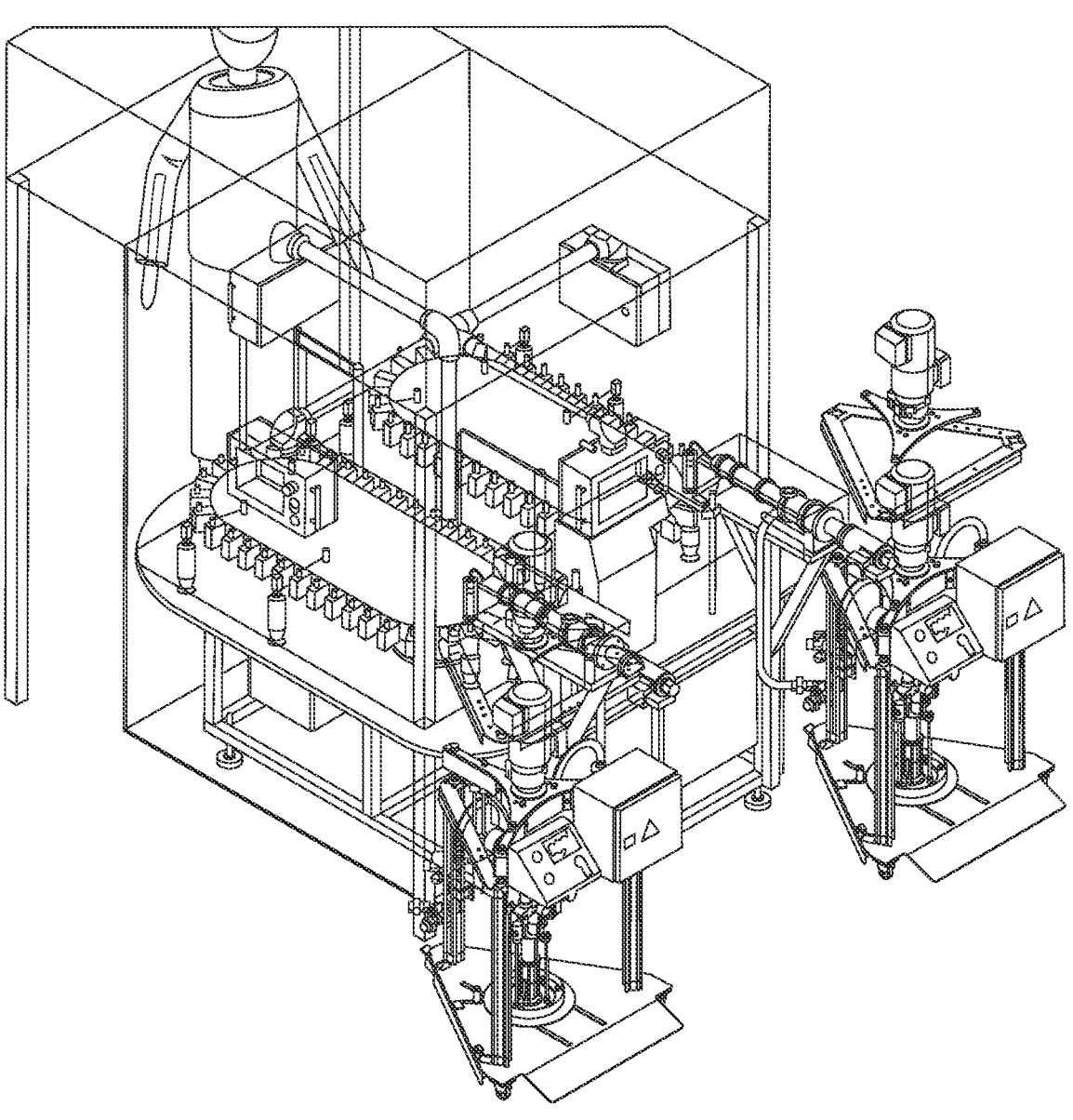
FIGS. 5 to 7: Schematic views of a machine enabling the preparation/dispense of a highly viscous gel characterized by an unending screw for mechanical pressure. Manipulation of the gel occurs under ambient conditions. The mechanical pressure permits conservation of the original viscosity of the gel.
Figure 6:
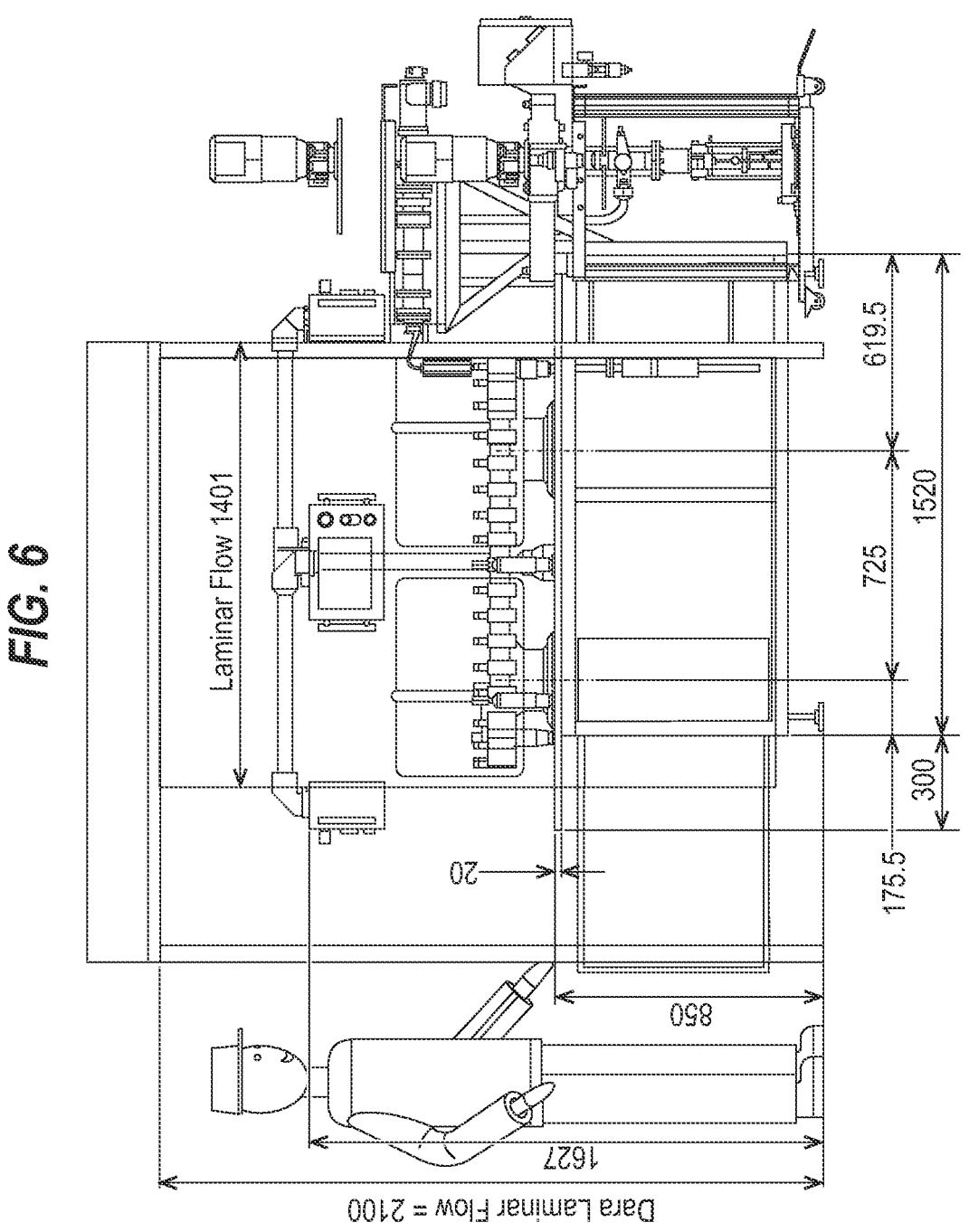
Figure 7:
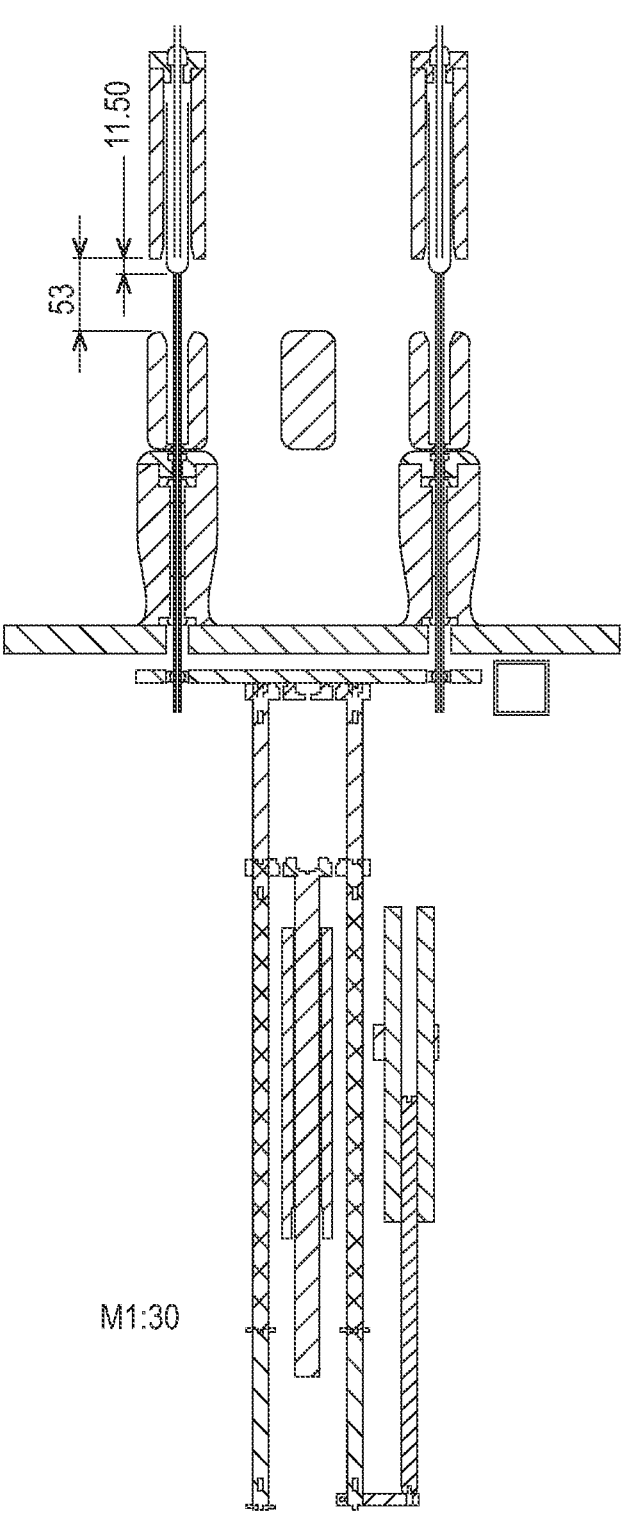
Figure 7:
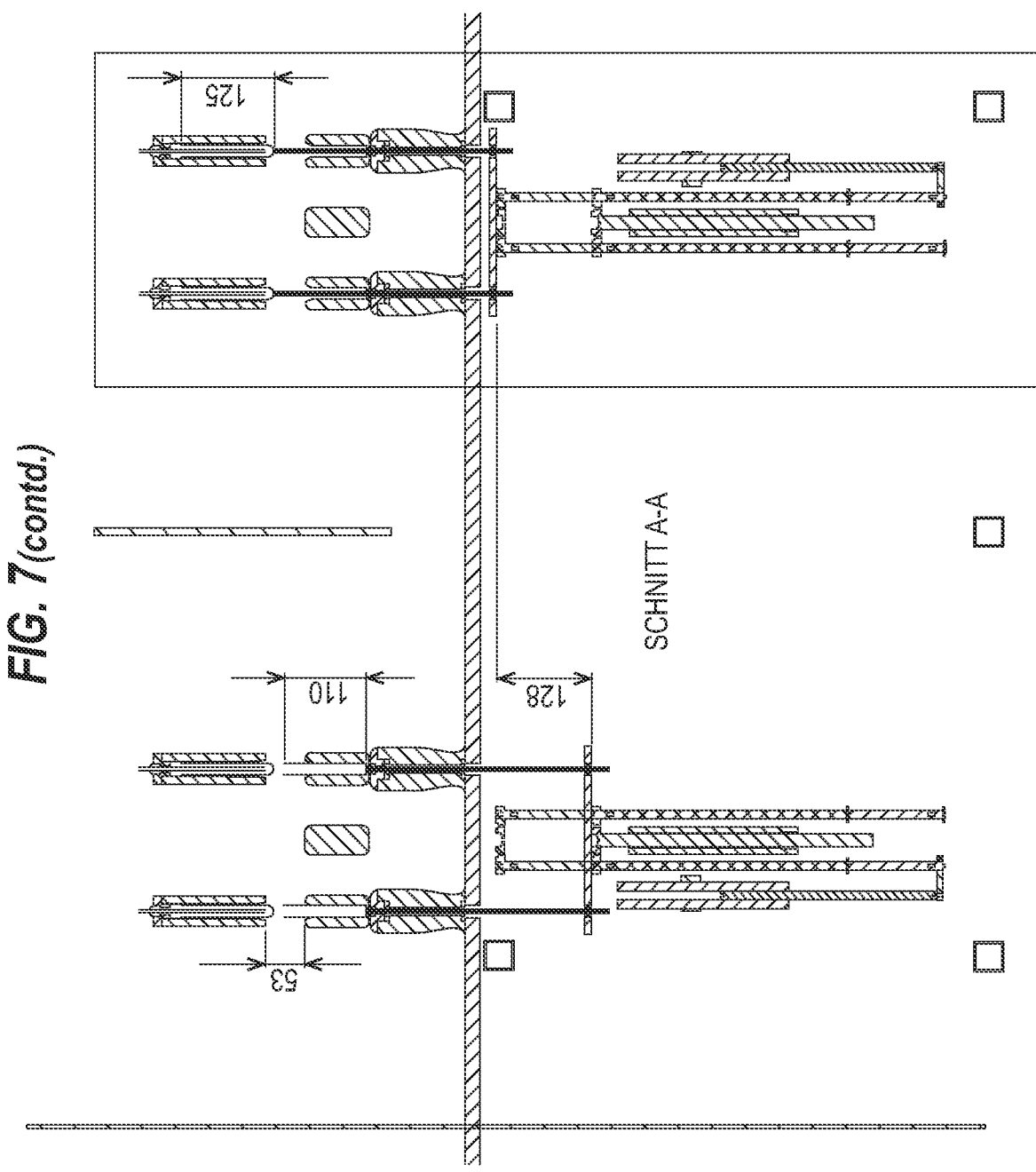

In one embodiment, the step of washing adipose tissue with a washing solution, preferably Phosphate-Buffered Saline (PBS) or physiological serum solution, is performed by a system as shown in FIG. 4 or FIG. 5, wherein one syringe contains the PBS or physiological serum solution and the other syringe contains the adipose tissue. Alternatively, in a preferred embodiment, such washing step is performed by using a multiple connector device as shown in FIG. 8 which advantageously allows mixing of multiple compositions via compartments, and enabling waste disposal, with the entire procedure performed in a closed circuit.

Figure 8:
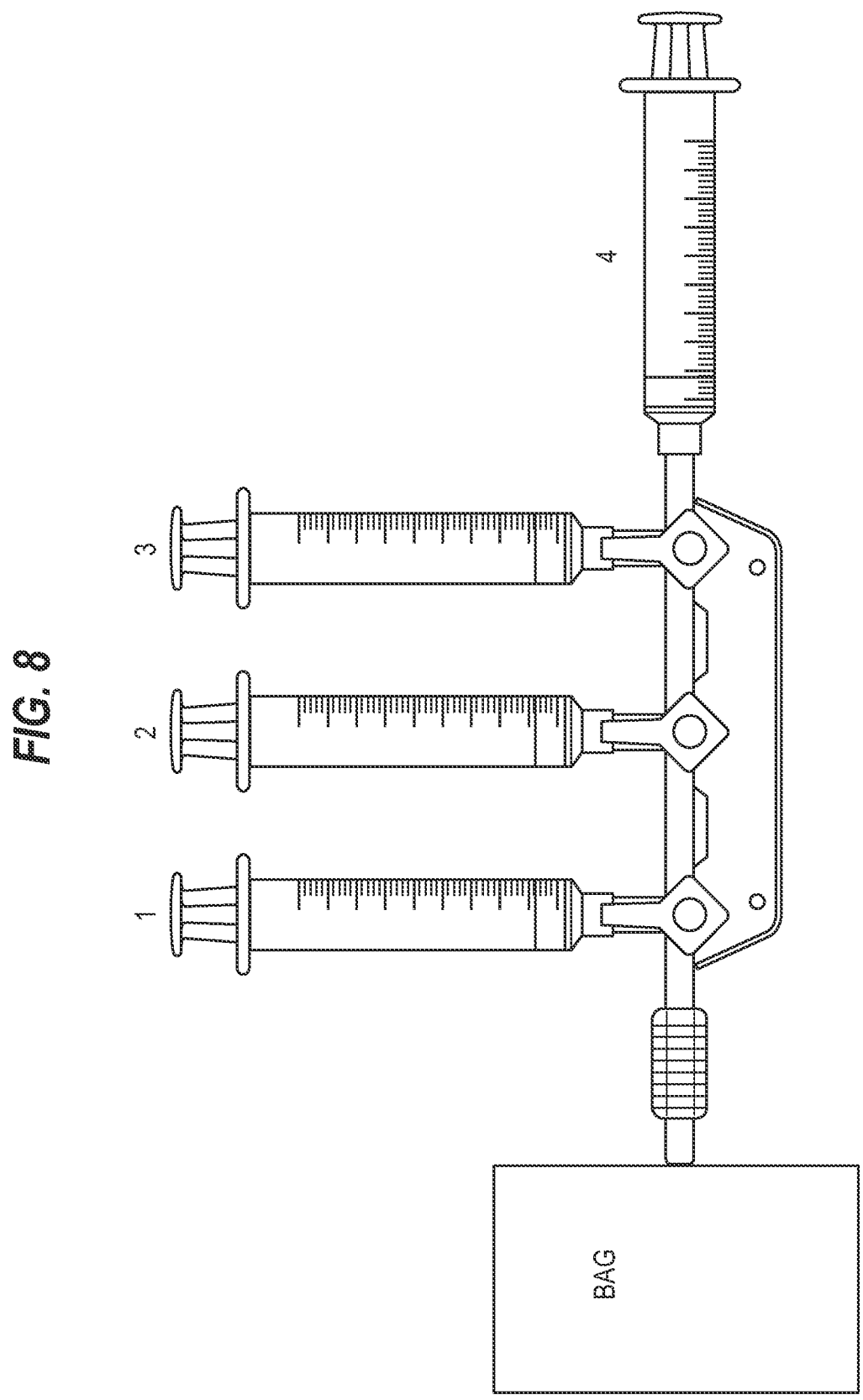
FIG. 8. Schematic view of a multiple connector device with multiple taps (for controlled release of flow) connected to various syringes (containing different compositions or substances to be mixed together simultaneously or sequentially) and a bag (e.g. for the collection of waste).

In another aspect, the invention provides a multiple connector device enabling the mixing of at the least 2, 3, 4, 5, 6 or more substances or compositions, characterized in that:

i) at the least 2, 3, 4, 5, 6 or more containers, preferably syringes, can be connected, preferably in closed circuit, into different separate locations of the multiple connector device (these separate locations corresponding to different inputs), see the embodiment in FIG. 8 with 4 syringes numbered 1 to 4 with therefore 4 inputs, ii) optionally at the least one bag, two bags, three bags, four bags, five bags, six bags or more for the collection of waste and/or collection of substances or compositions coming from one or more containers, simultaneously or in a sequential manner, wherein said bags are connected preferably in closed circuit; see the embodiment of FIG. 8 with only one bag connected to the multiple device connector; in one embodiment a bag may be connected to the multiple device connector for each container (in one embodiment we have five bags, bag 1 for syringe 1, bag 2 for syringe 2, bag 3 for syringe 3, bag 4 for syringe 5, and the bag as illustrated in FIG. 8; the bags may be located on the opposite side of the syringes, in direct continuation or between 2 syringes; such bags may collect waste from 1 syringe only, or preferably the waste coming from 2 or more syringes, preferably 2 syringes)

iii) optionally at the least one device, two devices, three devices, four devices, five devices, six devices or more, such device(s) being preferably a tap, located on said multiple connector device:

a. at the extremity of each container of i) on the multiple connector device as for example illustrated in FIG. 8 and/or (either or combination of)

b. between the containers of i) on the multiple connector device wherein such devices enable control of the release of the compositions or substances contained in the various containers (e.g. syringes) which also advantageously enables compartmentation (segmentation) of different areas of the multiple connector device in the case such devices are for example located between each container (e.g. equal distance between to containers on the multiple connector device).

Advantageously, a tap at the extremity of a container enables control release of the composition or substance contained in said syringe, whereas a tap between two syringes enable flux control of compositions or substances derived from 2, 3, 4, 5, 6 or more containers (flux control of mix of different compositions or substances from various containers or syringes).

The syringes may vary in from and size. Volume of syringes may also vary from e.g. 1 ml to 60 ml capacity.

In one embodiment, the device or tap is located on the multiple connector device between syringe 2 and syringe 3 of FIG. 8 which enables compartmentation/segmentation of syringes 1 and 2 from syringes 3 and 4 of FIG. 8 which enables control of flow. Advantageously, operator can therefore decide to stop or enable flow between these two compartments, or even a controlled flow (from weak to strong outflow between compartments). Advantageously, the operator may therefore in one embodiment mix together sequentially but preferably simultaneously (i) substances or compositions contained in syringes 1 and 2, and (ii) substances or compositions contained in syringes 3 and 4, without that substances or compositions contained in syringes 1, 2, 3 and/or 4 are mixed together.

In one embodiment, these compartments can even be separated or joined together with a connector device. In other words, in one embodiment, multiple connector devices may be joined together, e.g. a multiple connector device enabling connection of two containers is connected with another identical multiple connector device in order to get an assembled multiple connector device with possibly four containers connected). This has the advantage for the operator of processing separately the multiple connector devices for specific required steps and assembling them thereafter for a step requiring for example mixing of substances or compositions that were contained in containers located on separate multiple connector devices. In one embodiment, the tap enables a "on/off" mode (either full release or no release at all) or allows a precise control of the release or outflow of the composition or substance contained in each container (syringe) from an open (full release) to a closed position (no release at all).

Substances or compositions that may be present in the containers or syringes are PC, PRP, biomaterial, PC combined with hyaluronic acid, hyaluronic acid, PC combined with chitosan, PC combined with silk, chitosan, silk protein, fibroin, anticoagulant, a PC or BMC preservation solution, plasmalyte-A, a coagulation activator, thrombin serum, tricalcium phosphate (TCP), a bone substitute, calcium gluconate, calcium saccharate, growth factors, mannitol, collagen, albumin, ascorbic acid, biological tissue with stem cells (e.g. fat tissue), biological fluid with stem cells (e.g. bone marrow concentrate), cream, fat cells, stem cells, bone marrow concentrate, lubricin, cd-gelatin, botulinum toxin and/or one or more cell extracts, preferably an autologous cell extract, selected e.g. from an extract of keratinocytes, bone marrow, fibroblasts, periosteum or corneal cells, melanocytes and Langerhans cells, fat cells, muscle cells such as myoblasts and satellite cells, osteoblasts, chondrocytes, umbilical cord cells, mesenchymal stem cells (MSCs), preadipocytes, adipocytes, pre-endhotelial cells, Schwann cells or Achilles tendon cells.

Embodiments of different possible configurations for substances or compositions contained in the different containers or syringes to be connected to a multiple connector device are herein defined. The invention encompasses other types of configurations.

In one embodiment, the multiple connector device is connected to three syringes with one bag, see FIG. 8, but with one syringe less e.g. syringe 4. In this embodiment, 3 syringes are used numbered 1 to 3 and a bag (see FIG. 8). Syringe 1 contains a biomaterial preferably selected from hyaluronic acid, chitosan, silk protein or fibroin or any combination thereof, a platelet concentrate, PRP, BMC, or a combination of a biomaterial with a platelet concentrate (PRP), preferably PRP with hyaluronic acid. Syringe 2 contains a biological tissue with stem cells (e.g. fat tissue), biological fluid with stem cells (e.g. bone marrow concentrate), fat cells, stem cells, bone marrow concentrate and/or one or more cell extracts, preferably an autologous cell extract, selected e.g. from an extract of keratinocytes, bone marrow, fibroblasts, periosteum or corneal cells, melanocytes and Langerhans cells, fat cells, muscle cells such as myoblasts and satellite cells, osteoblasts, chondrocytes, umbilical cord cells, mesenchymal stem cells (MSCs), preadipocytes, adipocytes, pre-endhotelial cells, Schwann cells or Achilles tendon cells. Syringe 3 contains a washing solution like PBS or physiological serum. In this embodiment, the washing solution is used to wash the substance or composition contained in syringe 2, preferably a fat tissue composition containing stem cells, wherein waste is collected in the bag as illustrated in FIG. 8. Once the substance or composition contained in syringe 2 is washed, it is mixed with the composition of syringe 1, preferably PRP. The composition in syringe 1 may be a diluted composition, ranging from 20% to 80%, e.g. 20% to 80% PRP. The process of mixing the composition or substance of syringe 2 with the one of syringe 1 may be referred to as enrichment in the present invention. In one embodiment, the washed fat tissue of syringe 2 is mixed with a PRP of syringe 1. Once mixing is performed (10 seconds, 20 seconds, 30 seconds, 40 seconds, 1 minute, 2 minutes or more) then the resulting composition comprising PRP and fat tissue may be applied on or injected into humans or animals. Such resulting compositions may herein be referred to as a wound or tissue healing composition.

In another embodiment, the multiple connector device is connected to four syringes with one bag, see FIG. 8. In this embodiment, 4 syringes are used numbered 1 to 4 and a bag (see FIG. 8). Syringe 1 contains a coagulation activator like calcium gluconate, thrombin serum, preferably autologous thrombin serum or a combination of calcium gluconate with autologous thrombin serum. Syringe 2 contains a biomaterial preferably selected from hyaluronic acid, chitosan, silk protein or fibroin or any combination thereof, a platelet concentrate, PRP, BMC, or a combination of a biomaterial with a platelet concentrate (PRP), preferably PRP with hyaluronic acid. Syringe 3 contains a biological tissue with stem cells (e.g. fat tissue), biological fluid with stem cells (e.g. bone marrow concentrate), fat cells, stem cells, bone marrow concentrate and/or one or more cell extracts, preferably an autologous cell extract, selected e.g. from an extract of keratinocytes, bone marrow, fibroblasts, periosteum or corneal cells, melanocytes and Langerhans cells, fat cells, muscle cells such as myoblasts and satellite cells, osteoblasts, chondrocytes, umbilical cord cells, mesenchymal stem cells (MSCs), preadipocytes, adipocytes, pre-endhotelial cells, Schwann cells or Achilles tendon cells. Syringe 4 contains a washing solution like PBS or physiological serum. In this embodiment, the washing solution is used to wash the substance or composition contained in syringe 3, preferably a fat tissue composition containing stem cells, wherein waste is collected in the bag as illustrated in FIG. 8. Once the substance or composition contained in syringe 3 is washed, it is mixed with the composition of syringe 2, preferably PRP. The composition in syringe 2 may be a diluted composition, ranging from 20% to 80%, e.g. 20% to 80% PRP. The process of mixing the composition or substance of syringe 3 with the one of syringe 2 may be referred to as enrichment in the present invention. In one embodiment, the washed fat tissue of syringe 3 is mixed with a PRP of syringe 2. Once mixing is performed (10 seconds, 20 seconds, 30 seconds, 40 seconds, 1 minute, 2 minutes or more) then the resulting composition comprising PRP and fat tissue may then be mixed with the composition or substance of syringe 1 (e.g. calcium gluconate, autologous thrombin serum or combination thereof). This final mixing will enable coagulation activation of the PRP. The resulting composition (e.g. PRP, fat tissue and coagulation activator) may be applied on or injected into humans or animals. Such resulting compositions may herein be referred to as a wound or tissue healing composition.

In one embodiment of the invention, all the aforementioned methods use in part or only the multiple connector device for mixing substances or compositions (contained in individual containers or syringes), for processing any of the substances or compositions (contained in individual containers or syringes) e.g. enzymatic processing, washing processing and the like and/or for any waste removal.

In another aspect, the invention provides a cannula for tissue (e.g. fat) processing as shown in FIG. 9 and FIG. 10. Such cannula may herein be interchangeably referred to as a "tissue harvesting cannula" or "liposuction cannula". In another aspect, the invention provides a tissue harvesting or liposuction cannula comprising:

a) a cannular tube having a distal end and a proximal end, the proximal end of the cannular tube being insertable in tissue or cavity;

b) a plurality of peeling apertures each characterized by a spiral hole or spiral aperture (or snail hole or aperture).

Such spiral holes or apertures may be obtained by (see FIGS. 10.B and 10.C):

(i) making holes on the cannular tube, and (ii) crushing or pushing the cannula tube in two opposite sites simultaneously with sites perpendicular to the axis of each hole.

In another embodiment, spiral or snail holes or apertures may be characterized by decreasing radius. Spiral or snail holes or apertures may be characterized in that:

i) crushing sites are located nearer to the axial hole in comparison with the rest of the cannular tube, or in that they have a smaller diameter than rest of the cannular tube; and/or ii) virtual prolongation of one edge of the aperture will be beneath the other edge of the aperture.

Advantageously, such spiral or snail holes enable an atraumatic guided peeling of biological tissue. Such structure enables the collection of thin layers of biological tissue preserving the integrity of cells (atraumatic collection) corresponding to a soft harvesting or soft peeling, and soft liposuction in the case of fat tissue. Such layers may be considered as tissue (fat) grains or tatters. This also enables easier transfer of the biological tissue to a container or syringe connected to the cannula (see FIG. 9), as the peeled biological tissue is progressively shifted to the distal end of the cannula by incoming peeled biological tissue.

In another embodiment, the cannula may further be characterized in that the apertures are located at the proximal end of the cannula, all located in ⅓, ¼ or ⅕ of the proximal end of the cannula (see FIG. 10). In one embodiment, the cannula possesses three, four, five, six, seven, eight, nine, ten, eleven, twelve or more apertures, preferably five apertures. Advantageously, this enables localized peeling of biological tissue representing an appropriate surface for tissue harvesting. Further, advantageously, this enables also profound collection into surgical site of biological tissue (as located at the proximal end).

In another embodiment, the cannula may further be characterized in that the apertures are all arranged axially, radially and/or or angularly. Preferably, the apertures or holes are arranged in a helical manner (FIG. 10). An angle of about 30°, 32°, 34°, 36°, 38° or 40, preferably 36° separates each holes or apertures. Advantageously, such configuration of holes or apertures further enable atraumatic tissue harvesting. This also enables easier transfer of the biological tissue to a container or syringe connected to the cannula (see FIG. 9), by easier progression of the biological tissue to the distal end of the cannula.

In another embodiment, the cannula may be further characterized in that a suction hose may be connected to the distal end of the cannula in order to aspirate the peeled biological tissue.

In another embodiment, the cannula (e.g. fat harvesting cannula) may be connected to a container or syringe, preferably in closed circuit, wherein the thin layers of biological tissue are finally collected for further processing (FIG. 9). Such syringe of FIG. 9 may be connected for example to the multiple connector device of FIG. 8. The harvesting of the biological tissue from the proximal end of the cannula to said connected container or syringe may be enhanced by mechanical aspiration from the container or syringe, and/or by automated aspiration by the use of an aspiration tube and/or by vacuum inside the container or syringe.

The size of the apertures may be of about 10 mm, distance between each aperture or hole of about 4 mm, with entire cannula of about 170 mm, outer diameter of cannula of 2.5 mm, inner diameter of cannula of 2.1 mm (see FIG. 10).

In another embodiment, holes of the cannula may be deformed by spreading the corners of the holes (FIG. 10.D).

In one embodiment, the peeling apertures may be closed individually or separately by the operator. In another embodiment, the peeling apertures may be closed progressively by the operator (e.g. surgeon) by using e.g. a sliding device from the distal to the proximal end of the cannula. The more the sliding device is pushed to the proximal end of the cannula, the more apertures are closed. In such embodiment, the operator may close from the distal end the first aperture only, the first two apertures, the first three apertures, the four first apertures or all the apertures when collection of fat is terminated. This has the advantage of procuring flexibility to the operator depending on the size of the area to be harvested (if size important then all apertures are opened; if only a small harvesting area is required a few apertures may be closed). In such embodiments where apertures may be closed, the cannular tube may contain more apertures or apertures over the whole tube in contrast to FIG. 10.

In another aspect, the invention provides a composition (e.g. i) PRP/biomaterial with ii) fat tissue/biological tissue or biological fluid; or i) PRP/biomaterial, ii) fat tissue/biological tissue/fluid with iii) coagulation activator) obtained by using one or more of the said multiple connector device(s) (e.g. as shown in FIG. 8) and/or said cannula (e.g. as shown in FIGS. 9 and 10).

In another aspect, the invention provides a method for the preparation of a composition, wound healing composition or tissue healing composition (e.g. i) PRP/biomaterial with ii) fat tissue/biological tissue or biological fluid; or i) PRP/biomaterial, ii) fat tissue/biological tissue/fluid with iii) coagulation activator) by using one or more of the said multiple connector device(s) (e.g. as shown in FIG. 8) and/or said cannula (e.g. as shown in FIGS. 9 and 10).

In another aspect, the invention provides use of a composition, wound healing composition or tissue healing composition (e.g. i) PRP/biomaterial with ii) fat tissue/biological tissue or biological fluid; or i) PRP/biomaterial, ii) fat tissue/biological tissue/fluid with iii) coagulation activator) in skincare, osteoarthritis, on joints, tendons and/or ligaments, therapy, dermatology, dentistry, orthopedics, sports medicine, cosmetics, esthetics, surgery, ophthalmology, mesotherapy, injections, infiltrations, subcutaneous applications, wound care, volume enhancement, volume corrections, mechanical support and/or visco-supplementation. Further uses as herein described.

In another aspect, the invention provides a medical device comprising or consisting of one or more of said cannula(s) (e.g. as shown in FIGS. 9 and 10). In another aspect, the invention provides a medical device comprising or consisting of one or more of said multiple connector device(s) (as shown in FIG. 8). In another aspect, the invention provides a medical device comprising or consisting of one or more of said multiple connector device(s) and one or more of said cannula(s). In another aspect, the invention provides a medical device comprising or consisting of one or more of said multiple connector device(s) and one or more of said syringes. In another aspect, the invention provides a medical device comprising or consisting of one or more of said cannula(s) and one or more syringes. In another aspect, the invention provides a medical device comprising or consisting of one or more of said multiple connector device(s) and one or more of said cannula(s) and one or more syringes. Further devices or containers may be included in said medical devices, like phlebotomy accessories, needles, container(s) and/or tube(s) as herein mentioned in relation with FIG. 8, container(s) and/or tube(s) prefilled with biomaterial (s), anticoagulant(s) and/or cell selector gel (e.g. tube(s) with thixotropic gel and anticoagulant or tube(s) with thixotropic gel, anticoagulant and hyaluronic acid).

In another aspect, the invention provides a method for the preparation of collyrium comprising the steps of:

i) Collecting whole blood in at the least one container or syringe according to any of the previous aspects or embodiments, preferably by
  a. performing a venous puncture preferably using a butterfly needle connected to a collection holder,
  b. optionally piercing the stopper of a container to fill it with the whole blood using an internal needle of a collection system. Preferably, a vacuum within the container will enable automatic collection of the necessary volume of blood, e.g., about 8 ml,
  c. optionally carefully turning the container upside down preferably several times,
  d. optionally closing the blood collection needle with preferably a safety-Lock system,
ii) Centrifuging, preferably during about 5 minutes to about 10 minutes, preferably at a centrifugal force of about 1500 g, iii) Optionally homogenizing of PC, preferably by gently inverting the container several times, preferably re-suspending the cellular deposit in the supernatant (about 4 ml of PC may be obtained),
iv) Optionally preparing a collyrium containing the PC or BMC preferably in a single use drip dispenser, preferably by:
  a. drawing PC from a PC container preferably using at least one syringe (e.g. 5 ml) and at the least one transfer device,
  b. transferring PC to a collyrium container preferably by connecting at the least one cannula to the syringe,
  c. fixing or putting a dispenser into the container and optionally sealing the dispenser with container.

In another aspect, the invention provides a method for the preparation of calcium gluconate in combination with PC comprising the steps of:

i) Collecting whole blood in at the least one container or syringe according to any of the previous aspects or embodiments, preferably by:
  a. performing a venous puncture preferably using a butterfly needle connected to a collection holder,
  b. optionally piercing the stopper of a container to fill it with the whole blood using an internal needle of a collection system. Preferably, a vacuum within the container will enable automatic collection of the necessary volume of blood, e.g., about 8 ml,
  c. optionally carefully turning the container upside down preferably several times,
  d. optionally closing the blood collection needle preferably with a safety-Lock system,
ii) Centrifuging, preferably during about 5 minutes to about 10 minutes, preferably at a centrifugal force of about 1500 g,
iii) Optionally homogenizing of PC, preferably by gently inverting the container several times, preferably re-suspending the cellular deposit in the supernatant (about 4 ml of PC may be obtained),
iv) Collecting the PC in a syringe (e.g. 3 ml) preferably by screwing to a transfer device,
v) Optionally adding calcium gluconate to the PC by preferably connecting a needle (17G) to the PC syringe and preferably add about 10% to about 30% of calcium gluconate. Preferably the PC with calcium gluconate is homogenized in the syringe, preferably by gently inverting it.

In another aspect, the invention provides a method for the preparation of BMC in combination with PC and/or thrombin serum (e.g. ATS) comprising the steps of:

i) taking medullary blood using at the least one syringe, preferably in sterile field,
ii) transferring into at the least one tube, preferably by connecting each syringe containing the medullary blood to a transfer device preferably by carefully putting it on the stopper of the tube and applying light pressure through a protective film (the blood will be drawn up directly by the tube enabling a final volume of around 8 ml),
iii) optionally repeating this procedure to fill each available tube,
iv) optionally, once filling is complete, applying a self-adhesive disc to plug the hole in the protective film covering a tube,
v) optionally inverting the tube gently to obtain homogenous diffusion of the anticoagulant,
vi) Centrifuging the tube(s) preferably with two centrifugations with first centrifugation at about 2600 g during about 2 minutes and the second centrifugation at about 2000 g during 6 minutes (after centrifugation, the medullary blood is fractionated, the red blood cells are trapped under the gel, and the cellular elements settle on the surface of the gel), vii) preparing the final volume of medullary concentrate, preferably by handling the tube(s) carefully, preferably by:

a. optionally removing the protective film maintaining the sterility of the tube(s), b. optionally drawing, preferably gently, the excess supernatant (about 2 ml) using preferably a syringe fitted with a cannula by piercing the stopper of the tube, c. optionally inverting, preferably gently, the tube(s) to resuspend the cells settled on the gel, d. withdrawing the cellular concentrate using a syringe preferably fitted with a transfer device.

viii) Simultaneously or sequentially of the previous steps preparing of PC with optionally autologous thrombin serum (ATS), comprising the steps of:

vi) collecting whole blood in at the least one container or syringe according to any of the previous aspects or embodiments, preferably by:

a. performing a venous puncture preferably using a butterfly needle connected to a collection holder, b. optionally piercing the stopper of a container to fill it with the whole blood using an internal needle of a collection system. Preferably, a vacuum within the container will enable automatic collection of the necessary volume of blood, e.g., about 8 ml, c. optionally carefully turning the container upside down preferably several times, d. optionally closing the blood collection needle preferably with a safety-Lock system, e. optionally repeating the same procedure for the collection of ATS, vii) Centrifuging, preferably during about 5 minutes to about 10 minutes, preferably 9 minutes, preferably at a centrifugal force of about 1500 g (in the PC/BMC tube, after centrifugation, the blood is fractionated and cellular elements settle on the surface of the gel in the tube(s); in the ATS tube, after centrifugation, a clot settles on the gel, the liquid part constitutes activated thrombin serum), and viii) Optionally homogenizing of PC, preferably by gently inverting the container several times, preferably re-suspending the cellular deposit in the supernatant (about 4 ml of PC may be obtained), ix) Collecting of PC and/or ATS solutions and mixing the solutions, preferably by:

a. Taking the PC inside the tube(s) preferably using a syringe fitted with a transfer device (8), and/or b. taking the supernatant fluid serum (autologous thrombin serum) inside the ATS tube preferably using an about 1 ml sterile syringe fitted with a cannula (e.g. 80 mm), c. optionally mixing the all the preparations.

The biomaterial, hyaluronic acid and/or chitosan, polymer and/or anticoagulant may be prefilled sequentially or simultaneously, optionally during the manufacturing process, optionally by one or more injectors. Preferably, the hyaluronic acid and/or chitosan, polymer and/or anticoagulant are prefilled sequentially.

In another aspect, the invention provides a method of automatically manufacturing containers or syringes according to any aspects or embodiments of the invention comprising:

a. filling container(s), tube(s), or syringe(s) with either:
    i. an anticoagulant,
    ii. a polymer and an anticoagulant,
    iii. a biomaterial and an anticoagulant, or
    iv. a biomaterial, a polymer and an anticoagulant, b. optionally allowing controlled vacuum and/or clogging of the container(s), tube(s), or syringe(s).

A cell selector gel may herein be referred to as a polymer.

Other substances described herein may be combined during one or more of the steps of a manufacturing method of the invention.

In another aspect, the invention provides a method of automatically manufacturing containers or hematology tubes by means of a filling machine comprising controlled vacuum and clogging of the containers or hematology tubes.

In one embodiment, the containers or syringes according to any aspects or embodiments of the present invention are prefilled with a substance selected from agar, gelose, collagen, chitosan, growth factors, ascorbic acid, albumin, fibroin, silk protein or fibroin-fibroin proteins or hyaluronic acid.

Agar, gelose, collagen, ascorbic acid, albumin, silk protein or fibroin-fibroin proteins may all display stabilizing and/or viscosity properties useful for a composition of the present invention. In one embodiment, hyaluronic acid or chitosan may be substituted by or combined with agar, gelose, collagen, ascorbic acid, albumin, fibroin and/or silk protein or fibroin-fibroin proteins. Preferably, hyaluronic acid or chitosan may be substituted by or combined with fibroin or silk protein or fibroin-fibroin proteins. In one embodiment, fibroin or silk protein or fibroin-fibroin proteins may be combined with PC and/or BMC. In another embodiment, fibroin or silk protein or fibroin-fibroin proteins may be combined with chitosan and/or HA in combination with PC and/or BMC. In another embodiment, albumin may be combined with PC and/or BMC. In another embodiment, albumin may be combined with chitosan and/or HA in combination with PC and/or BMC. In another embodiment, albumin may be combined with chitosan and/or HA, silk protein or fibroin-fibroin proteins, and further combined with PC and/or BMC.

In one embodiment, a substance selected from agar, gelose, collagen, chitosan, growth factors, ascorbic acid, albumin, fibroin, silk protein or fibroin-fibroin proteins or hyaluronic acid, and/or any combination thereof may be prefilled in containers or syringes according to any aspects or embodiments of the present invention.

In one embodiment, instead of or in combination with hyaluronic acid, a similar substance may be used or combined, for example gelose, agar, collagen chitosan, albumin and/or silk protein or fibroin-fibroin proteins, and/or any combinations thereof.

Preferably, the anticoagulant is citrate or sodium citrate.

Preferably, the polymer is a thixotropic gel.

Preferably, the container, tube, syringe, kit or device is for human use or human treatment. In one embodiment, the container, tube, syringe, kit or device may be used for animals, or adapted for veterinary use or animal treatment.

Preferably, the method of manufacturing according to any of the previous aspects is performed under laminar flow and/or bioburden controlled.

The containers, tubes or syringes may be of different shapes and made of crystal, glass, plastic or metal. Preferably, the containers, tubes or syringes are made of plastic, preferably COP or COC, preferably without phtalates.

In another embodiment, the invention provides hyaluronic acid (HA) of about 1000

KDa to about 2000 KDa at about 1.5% to about 2.5% concentration, of about 1400 KDa to about 1600 KDa at about 1.8% to about 2.2% concentration, of about 1550 KDa at about 1.8% to about 2.2% concentration, more preferably from about 1.7% to about 2% concentration. Such HA are particularly adapted for injections or infiltrations, intra dermal injections, subcutaneous applications, intra-articular infiltrations, fistulas and/or as a biological glue.

Such compositions of hyaluronic acid of are also particularly adapted for a combination with a platelet concentrate, preferably a platelet rich plasma (PRP).

In another aspect the invention provides hyaluronic acid of about at least 4000 KDa (about 4000 Kda or above 4000 KDa) at about 1.5% to about 2.5% concentration, of about at least 4000 KDa (about 4000 KDa or above 4000 KDa) at about 1.8% to about 2.2% concentration, more preferably of about 4000 KDa at about 2% concentration, hyaluronic acid of about 4000 KDa to about 6000 KDa at about 1.8% to about 2.2% concentration. Such compositions are particularly adapted for mechanical support, for intra dermal injections, subcutaneous applications, volumetric corrections and or visco-supplementation.

In one embodiment, the present invention encompasses a combination of at least two hyaluronic acids differing in molecular weight and in concentration.

In another aspect, the invention provides a hyaluronic acid composition comprising at least one low molecular weight hyaluronic acid and at least one high molecular weight hyaluronic acid characterized in that:

the low molecular weight hyaluronic acid is less than 600 KDa or about 600 KDa, and the high molecular weight hyaluronic acid is about 4000 Kda or above 4000 KDa (about at least 4000 KDa).

In another aspect, the invention provides a hyaluronic acid composition comprising one low molecular weight hyaluronic acid and one high molecular weight hyaluronic acid characterized in that:

the low molecular weight hyaluronic acid is less than 600 KDa or about 600 KDa, and the high molecular weight hyaluronic acid is about 4000 Kda or above 4000 KDa (about at least 4000 KDa).

At least one hyaluronic acid has a molecular weight of less than 600 KDa or a molecular molecular weight of about 600 KDa, and at least one hyaluronic acid has a molecular weight of more than 4000 KDa or a molecular molecular weight of about 4000 KDa. In one embodiment, at least one hyaluronic acid has a molecular weight of about 400 KDa to about 600 KDa, and at least one hyaluronic acid has a molecular weight of about 4000 KDa to about 6000 KDa.

HA may be reticulated or non reticulated.

Preferably, the respective ratio is about 2:3 (low molecular weight hyaluronic acid to high molecular weight hyaluronic acid; i.e. hyaluronic acid of less than 600 KDa or about 600 KDa to hyaluronic acid of more than 4000 KDa or about 4000 KDa) with a total concentration of about 2.2% to about 2.8%. Alternatively, the respective ratio is about 8:5 with a total concentration of about 3% to about 3.5%. Such formulations are particularly adapted for mechanical support, for intra dermal injections, subcutaneous applications, volumetric corrections and or visco-supplementation.

Advantageously, such hyaluronic acid combinations procure suitable viscosity for manipulation. Advantageously, in the combination of HA differing in molecular weight, a high molecular weight HA may increase viscosity suitable for mechanical support and a low molecular weight HA may contribute to cell proliferation/regeneration by protecting cells and their activity.

Chitosan may be particularly suitable in a combination with HA and/or a platelet concentrate for its stabilizing properties and viscosity maintenance. Chitosan may further enhance the stability and/or efficiency of a PRP-HA composition. Moreover, chitosan has coagulation properties at physiological temperature, i.e. around 37° C. The coagulation properties are absent at room temperature making chitosan particularly useful for human use. Advantageously, no other coagulation activator than chitosan may be required in a formulation of the present invention. Chitosan may therefore not only be useful for its stabilization and viscosity maintenance properties, but also as coagulation activator. Chitosan may therefore be particularly useful for all formulations requiring a coagulation activator as for the preparation of platelet rich plasma. The presence of chitosan makes such formulation particularly suitable for all indications or treatments involving the cartilage. In one embodiment of the present invention, a coagulation activator of the present invention may be substituted or combined with chitosan.

HA or chitosan may herein be substituted or combined with fibroin and/or silk protein or fibroin-fibroin proteins or any other biomaterial.

Preferably, hyaluronic acid is located at the bottom of the tube or syringe, followed by a thixotropic gel and above an anticoagulant, preferably sodium citrate.

The anticoagulant of the present invention may be citrate, for example a buffered sodium citrate solution at about 0.10 M or an anhydrous sodium citrate at about 3.5 mg/mL. Preferably, sodium citrate is at about 0.109M.

In a preferred aspect, the invention provides a container, preferably a tube, comprising about 2.0 g of hyaluronic acid 1550KDa, about 1.9 g of polymer gel (thixotropic gel), and about 0.7 ml sodium citrate solution at about 0.109M.

Preferably, the container, preferably a tube, contains about 1 ml to about 2 ml of hyaluronic acid, about 2 g of cell selector or thixotropic gel and about 1 ml of sodium citrate at 0.109M.

In further embodiments, the invention provides a container, preferably a tube, which may be used for the preparation of a wound healant composition or tissue healant composition, selected from:

i) a glass separator tube comprising hyaluronic acid and/or chitosan, a polyester-based thixotropic gel and a buffered sodium citrate solution at about 0.10 M, ii) a polyethylene terephthalate separator tube comprising hyaluronic acid and/or chitosan, a highly thixotropic gel formed by a polymer mixture and an anhydrous sodium citrate at about 3.5 mg/m, iii) a Cyclic Olefin Copolymer (COC) or Cyclic Olefin Polymer (COP) separator tube comprising hyaluronic acid and/or chitosan, a polyester-based thixotropic gel and a buffered sodium citrate solution at about 0.10 M, or iv) a Cyclic Olefin Copolymer (COC) or Cyclic Olefin Polymer (COP) filter separator tube containing hyaluronic acid and/or chitosan, and a buffered sodium citrate solution at abut 0.10 M or an anhydrous sodium citrate at about 3.5 mg/mL.

Preferably, HA is mixed or concentrated, preferably at about 2%, in phosphate buffer (PBS).

In another aspect, the biomaterial, preferably HA, is steam sterilized. In one embodiment, the biomaterial, preferably HA, is steam sterilized from about 105° C. for about 8 minutes, to about 121° C. for about 20 minutes. Preferably, the biomaterial, preferably HA, is sterilized by steam at about 105° C. for about 8 minutes. In one embodiment, the container, syringe or tube comprising the HA formulation is steam sterilized.

In another aspect, the present invention provides a wound healant or tissue healant comprising a composition according to the invention.

In another aspect, the present invention provides a composition according to the invention for use in therapy.

In another aspect, the present invention provides a method or process for the preparation of a wound healant or tissue healant comprising a platelet concentrate or platelet-rich plasma or BMC, comprising the steps of:

a) Centrifuging whole blood or bone marrow in a container, preferably a container, tube or syringe according to the invention, and b) Collecting the wound healant or tissue healant comprising a platelet concentrate or platelet-rich plasma or BMC.

Preferably, the centrifugation step is performed at a force of or about 1500 g up to about 2000 g (this speed is with a radius of about 20 cm at about 2500 to about 3000 rpm). Preferably, the centrifugation step is performed in a sufficient length of time to form a barrier between the plasma containing the platelets, the lymphocytes and the monocytes and the gel containing the erythrocytes. Preferably, centrifugation time is about 3 minutes to about 15 minutes, preferably 5 minutes to about 10 minutes. In one preferred embodiment, centrifugation speed is about 1500 g with centrifugation time is of about 5 minutes or about 9 minutes. Centrifugation time and speed depends on the formulation present in the device. The skilled artisan can determine the appropriate centrifugation time and speed according to the composition used.

In one embodiment, the wound healant or tissue healant is separated from the full plasma by removing first about half of the supernatant containing the platelet poor plasma.

Optionally, after the centrifugation step, the platelet concentrate or platelet rich plasma is mixed with hyaluronic acid and/or chitosan.

Optionally, a cannula can be used in order to initiate the homogeneization. In order to obtain a higher cellular concentration, or a higher viscosity of the mix, before proceeding to the platelet resuspension, about 0.5 ml, about 1 ml or about 1.5 ml of the upper layer of the platelet poor plasma (PPP) supernatant may be delicately removed with a long cannula. Resuspending the cellular deposit in the remaining PRP by gentle inversions of the tube may then be performed (homogenization).

In another aspect, the invention provides a process or method for the preparation of a wound healant composition or tissue healant composition comprising a platelet concentrate or platelet-rich plasma or BMC, comprising the steps of:

a) Centrifuging whole blood or bone marrow in a container, tube or syringe according to the invention, b) Optionally removing platelet poor plasma, preferably about 1 ml of the upper layer of the platelet poor plasma, c) Optionally homogenizing the resulting composition and/or re-suspending the cellular deposit in the supernatant, preferably by inverting the container, tube or syringe, d) Collecting the wound healant or tissue healant comprising a platelet concentrate or platelet-rich plasma or BMC, e) Optionally further mixing said wound healant or tissue healant, f) Optionally further combining said wound healant or tissue healant with at least one additional substance and/or one or more cell extracts.

In another aspect, the present invention provides a wound healant or tissue healant composition prepared according to a method of the present invention.

Preferably, a container, a tube or syringe, according to the invention is used in a method or process according to the invention. Preferably, the container, tube or syringe does not contain phthalate.

In one embodiment, the wound healant or tissue healant may be combined with at least one additional substance such as a coagulation activator, thrombin serum, tricalcium phosphate (TCP), a bone substitute, hyaluronic acid composition, calcium gluconate, calcium saccharate, chitosan, fibroin, silk protein or fibroin-fibroin proteins, growth factors, mannitol, collagen, albumin, ascorbic acid, cream, fat cells, fat tissue, bone marrow concentrate, lubricin, cd-gelatin, botulinum toxin and/or one or more cell extracts, preferably an autologous cell extract, preferably a cell extract selected from an extract of keratinocytes, bone marrow, fibroblasts, periosteum or corneal cells, melanocytes and Langerhans cell; fat cells, muscle cells such as myoblasts and satellite cells; osteoblasts; chondrocytes; umbilical cord cells; stem cells, mesenchymal stem cells (MSCs), preadipocytes, pre-endhotelial cells, Schwann cells, glial cells, neurones or Achilles tendon cells.

In one embodiment, calcium gluconate at about 1% to about 10% may be added for appropriate coagulation of the infected site. In one embodiment, calcium chlorure may be used. More preferably, calcium gluconate at about 10% may be used. Alternatively, calcium saccharate may be used. In one embodiment, a combination of calcium gluconate and calcium saccharate may be used. For example, fora 100 ml of solution, about 9.5 g of Calcium gluconate and about 360 mg of Calcium saccharate may be used. For example, for a 2 ml single dose ampoule about 0.19 g of calcium gluconate and about 7.2 mg calcium saccharate may be used for a calcium content of about 0.463 mmol per 2 ml ampoule. For example, for a 5 ml single dose ampoule, about 0.47 g of calcium gluconate and about 18 mg calcium saccharate may be used for a calcium content of about 1.148 mmol per 5 ml ampoule. The skilled artisan will easily determine the appropriate calcium content according to the specific use.

The compositions or formulations of the present invention provide a volume effect, with desirable long term outcome on skin. Cells are being smoothed or flattened. Fibroblasts are stimulated, the activity of fibroblasts are being protected. The compositions or formulations of the present invention allows maintenance of fibroblast's structure.

Formulations may be adapted to a specific use. For injection and/or infiltration, the formulations may be used without additional substance as a viscous formulation.

As other useful applications to the skilled artisan/surgeon, a biological glue may be obtained with PC, A-PRP or PRP in combination with a biomaterial without additional substances. The dispensation requires the use of a dual dispenser that allow the formation of the glue when the PC plus biomaterial substances are injected simultaneously into the surgical site. In one embodiment, a dual dispenser may be used for the injection of a formulation of the present invention.

In order to obtain a stronger biological glue, the compositions or formulations of the present invention may be combined with a coagulation activator like a calcium salt, preferably CaCl2, or thrombin, preferably an autologous thrombin. Alternatively or in addition to CaCl2 or thrombin, the compositions or formulations of the present invention may be combined with calcium gluconate and/or calcium saccharate.

For other applications evident to the skilled artisan, a suturable membrane may be more suitable. In order to obtain a suturable membrane, the compositions or formulations of the present invention may be combined with a higher concentration of coagulation activator like an autologous or homologous thrombin, a calcium salt like CaCl2, but preferably Calcium Gluconate. Alternatively or in addition to CaCl2 or thrombin, the compositions or formulations of the present invention may be combined with TCP (TriCalcium Phosphate). The compositions or formulations of the present invention may be combined with TCP for deep injection and/or volume enhancement.

HA alone or a combination of HAs may be further combined with chitosan, collagen, albumin or other biomaterial. Chitosan may be from animal origin, for example crustacean, or vegetal origin, for example Paris mushroom.

Containers, tubes, syringes, compositions or medical devices of the present invention may be used as ophthalmic collyre (eyewash), in articulations (for example knee), sports medicine, muscular lesions or rotator cuff.

Containers, tubes, syringes, compositions or medical devices of the present invention may be used in esthetics, mesotherapy, wrinkle filling (superficial and profound), as a mask post laser, post peeling or monotherapy (for example glitter, gloss, brilliance or brightness) or erectile dysfunction.

Containers, tubes, syringes, compositions or medical devices of the present invention may be used in wound care, diabetic wounds or in large vascular wounds.

Containers, tubes, syringes, compositions or medical devices of the present invention may be used in ophthalmology.

The formulations or compositions may be combined and/or administered in several ways. In one embodiment, a formulation or composition according to the invention may be combined or mixed with PC in a procedure as described in WO2011/10948. WO2011/10948 is incorporated in full herein.

In another aspect, the invention provides a composition according to the invention further combined with a coagulation activator, thrombin serum, tricalcium phosphate (TCP), a bone substitute, hyaluronic acid composition, calcium gluconate, calcium saccharate, chitosan, fibroin, silk protein or fibroin-fibroin proteins, growth factors, mannitol, collagen, albumin, ascorbic acid, cream, fat cells, fat tissue, bone marrow concentrate, lubricin, cd-gelatin, botulinum toxin and/or one or more cell extracts, preferably an autologous cell extract, preferably a cell extract selected from an extract of keratinocytes, bone marrow, fibroblasts, periosteum or corneal cells, melanocytes and Langerhans cell; fat cells, muscle cells such as myoblasts and satellite cells; osteoblasts; chondrocytes; umbilical cord cells; stem cells, mesenchymal stem cells (MSCs), preadipocytes, pre-endhotelial cells, Schwann cells, glial cells, neurones or Achilles tendon cells.

In one embodiment, a coagulation activator, thrombin serum, cell selector gel, tricalcium phosphate (TCP), a bone substitute, hyaluronic acid composition, calcium gluconate, calcium saccharate, chitosan, fibroin, silk protein or fibroin-fibroin proteins, growth factors, mannitol, collagen, albumin, ascorbic acid, cream, fat cells, fat tissue, bone marrow concentrate, lubricin, cd-gelatin, botulinum toxin and/or one or more cell extracts or any combination thereof are pre-filled, injected or inserted in a container, tube or syringe according to any aspects of the invention.

In another aspect, the invention provides a container, syringe, tube or medical device according to the invention, wound healant composition, tissue healant composition, cell composition, composition, platelet concentrate composition, HA composition, chitosan composition, BMC composition, PRP composition, A-PRP composition, thrombin serum, or haemostatic agent obtained by using a container, tube, syringe or medical device according to any of the previous aspects or obtained by a method according to any of the previous aspects for use in dentistry, orthopedics, sports medicine, cosmetics, esthetics, surgery, ophthalmology and/or mesotherapy.

In another aspect, the invention provides the use of a container, syringe, tube or medical device according to the invention, wound healant composition, tissue healant composition, cell composition, platelet concentrate composition, HA composition, chitosan composition, BMC composition, PRP composition, A-PRP composition, thrombin serum, or haemostatic agent obtained by using a container, tube, syringe or medical device according to any of the previous aspects or obtained by a method according to any of the previous aspects for cellular regeneration, for tissue adhesion, for promoting wound healing or tissue healing and/or sealing and/or regeneration of a tissue and/or a cartilage and/or a bone and/or a nerve in a wound or tissue of a human or animal, or for inducing periodontal regeneration in a wound or a periodontal defect of a mammal with periodontal disease or other condition requiring periodontal regeneration, or for ligament and/or cartilage reconstitution, or for promoting skin regeneration in a scar or a wrinkle, or for increasing adipose tissue volume in a mammal with a dermal fat graft or other condition requiring adipose tissue regeneration, or for inducing myocardial regeneration in a mammal with myocardial deficiency or other condition requiring myocardial regeneration tissue regeneration, or for inducing corneal regeneration in a mammal with corneal deficiency or other condition requiring corneal regeneration, or for inducing articular or cartilage regeneration in a mammal with articular or cartilage deficiency or other condition requiring articular or cartilage tissue regeneration, or for promoting skin regeneration in a scar, a wrinkle or a fat deficiency from human or lower animal, or for inducing peripheral nerve regeneration in a mammal with peripheral nerve damage, nerve suture or spinal cord injury or other condition requiring peripheral nerve regeneration, or for inducing bone regeneration in a mammal with bone damage, bone deficiency or other condition requiring bone regeneration, or for injections for orthopedic and injections for esthetic, or for regeneration and/or rejuvenation of skin tissues, particularly in promoting and/or initiating skin regeneration such as reducing skin wrinkles, deep wrinkles, acne, burns, rubella or small pox scars, vitiligo and lipoatrophy, amelioration of nasolabial lines and treatment of skin damages or disorders such as skin burns, Kaposi's sarcoma, skin skeloids or Dupuytren's palmar fibromatosis and in the reduction of pain associated with skin and tissue regeneration, or for wound or tissue healing or regeneration treatments, especially the treatment of traumatic or surgical wounds such in the fitting and/or holding and/or sealing of native or prosthetic grafts; treatment of vasculitis; ulcers such as diabetic neuropathic ulcers or decubitus sores, diabetic ulcer, perforating ulcer or diabetic perforating ulcer, arthritis, osteoarthritis, pseudo-arthritis, radiodermatitis and closing fistulas, or for cardiac disorders, cardiac regeneration such as in the treatment of heart failure, chronic cardiac failure, ischemic and non-ischemic cardiac failure and cardiomyopathy, or for bone, cartilage and articular disorders such as chondral damage, cartilage and/or bone injury such as deep cartilage damage and/or erosion and/or arthroscopy, tendon torn and rotator cuff in shoulder, or for corneal disorders such as dry eye syndrome; corneal opacity such as those caused by chemical burns, affliction by Steven's Johnson syndrome; scarring of the cornea and corneal ulcers, or for peripheral nerve damage, nerve suture and spinal cord injury.

In another aspect, the invention provides the use of a container, syringe, tube or medical device according to the invention, wound healant composition, tissue healant composition, composition, cell composition, platelet concentrate composition, HA composition, chitosan composition, BMC composition, PRP composition, A-PRP composition, thrombin serum, or haemostatic agent obtained by using a container, tube, syringe or medical device according to any of the previous aspects or obtained by a method according to any of the previous aspects on a wound, a damaged tissue, damaged bone or periodontal defect or cavity.

In another aspect, the invention provides a use of a container, syringe, tube or medical device according to the invention, wound healant composition, tissue healant composition, composition, cell composition, platelet concentrate composition, HA composition, chitosan composition, BMC composition, PRP composition, A-PRP composition, thrombin serum, or haemostatic agent obtained by using a container, tube, syringe or medical device according to any of the previous aspects or obtained by a method according to any of the previous aspects for the manufacture of a medicament for healing of wounds or tissues or for promoting bone or periodontum growth and/or bone and/or tissue regeneration such as skin, cartilage, muscle, tendon, ligament, adipose tissue, cornea, peripheral nerves, spine or bone regeneration.

In another aspect, the invention provides the use of a container, syringe, tube or medical device according to the invention, wound healant composition, tissue healant composition, composition, cell composition, platelet concentrate composition, HA composition, chitosan composition, BMC composition, PRP composition, A-PRP composition, thrombin serum, or haemostatic agent obtained by using a container, tube, syringe or medical device according to any of the previous aspects or obtained by a method according to any of the previous aspects for the manufacture of a cosmetic preparation for use as anti-aging agent or skin repairing agent such as a scar repairing agent, lipoatrophy repairing agent, a wrinkle filling and/or repairing agent, for esthetic preparation, aging management, volume corrector and/or hair stimulator.

In another aspect, the invention provides the use of a container, syringe, tube or medical device according to the invention, wound healant composition, tissue healant composition, composition, cell composition, platelet concentrate composition, HA composition, chitosan composition, BMC composition, PRP composition, A-PRP composition, thrombin serum, or haemostatic agent obtained by using a container, tube, syringe or medical device according to any of the previous aspects or obtained by a method according to any of the previous aspects for the manufacture of a cosmetic preparation for use in dentistry, orthopedics, arthritis, osteoarthritis, pseudo-arthritis or else. In one embodiment, the wound healant composition or tissue healant composition is applied in a dental cavity, on a diabetic ulcer, perforating ulcer, diabetic perforating ulcer, or else.

In one embodiment, the wound healant composition, tissue healant composition, composition, cell composition, platelet concentrate composition, HA composition, chitosan composition, BMC composition, PRP composition, A-PRP composition, thrombin serum, or haemostatic agent may be combined with tricalcium phosphate (TCP), with any bone substitute and/or hyaluronic acid/chitosan preferably before the formation of the clot. The composition may be used as volume corrector (TCP at 10-30 microns), in dentistry, orthopedics (TCP at 50 microns).

Combinations include TCP, hyaluronic acid/chitosan and a PRP composition. A preferred combination includes TCP, hyaluronic acid/chitosan and an A-PRP composition. Combinations include TCP, hyaluronic acid, gelose, chitosan, albumin, mannitol, growth factors, ascorbic acid, collagen and/or silk protein or fibroin with an A-PRP composition or PRP composition.

The formation of a clot is a multi-step process or cascade and several of these steps require the presence of calcium ions. By removing the calcium ions present in whole blood, as is the effect when the blood is collected in citrate, the blood can be prevented from clotting. A calcium chelating agent (also referred herein as anticoagulant) is a chemical that reacts with the calcium, present in blood, in such a fashion that the calcium can no longer function in blood coagulation. The most common chelating agent is a salt of citric acid (citrate), since it has the fewest side effects on the components of the clotting system. By collecting blood into a medium containing a calcium chelating agent such as citrate, sample collection and further preparations of the citrated sample can be performed over a time period of up to several hours. Preferred calcium chelating agent is sodium citrate.

A buffered sodium citrate solution at about 0.10 M or an anhydrous sodium citrate at about 3.5 mg/mL may be used.

Alternatively, hirudin, benzylsulfonyl-d-Arg-Pro-4-amidinobenzylamide (BAPA), heparin, citrate, acid citrate dextrose (ACD), citrate-theophylline-adenosine-dipyridamole (CTAD) or potassium-ethylenediaminetetra-acid (EDTA) may be used as anticoagulants. Combination of anticoagulants may be used and injected in the hematology tubes via various or same injectors, sequentially or simultaneously.

In one embodiment, instead of thrombin serum, an alternative coagulation activator may be used such as calcium chloride or calcium saccharate, preferably calcium gluconate.

In one embodiment, multiple coagulation activators may be used in combination, preferably thrombin serum with calcium gluconate and optionally calcium saccharate.

Advantageously, the methods of the present invention permit manipulation of the blood in an entirely closed circuit during the entire process, from the manufacturing process, blood collection, manipulation till application or injection to the patient. All the devices and kits are therefore adapted for an entirely closed circuit manipulation in order to avoid direct contact of the blood and hematology tubes with air.

Further uses may include healing of wounds or for promoting bone or periodontum growth and/or bone and/or tissue regeneration.

Further uses may include the manufacture of a cosmetic preparation for use as anti-aging agent or skin repairing agent such as a scar repairing agent, a wrinkle filling and/or repairing agent.

Further uses may include the manufacture of a cosmetic preparation for use as esthetic preparation, aging management, volume corrector, wrinkle feeling, brown spot reduction and/or hair stimulator. Compositions may be applied on and/or around the eyes, lips, eyelids, face, neck, chest, scalp, hair, hands and all the rest of the body and/or male and female genitalia. In one embodiment, the cosmetic preparation and/or esthetic preparation is combined with a cosmetic agent, cosmetic cream or cosmetic mask. Further uses include aesthetics, for example as filler.

The present formulations may be applied on a mask.

Further uses may include ligament and/or cartilage reconstitution. Advantageously, ligament and/or cartilage reconstitution time using a composition of the present invention is divided by a factor 2 or 3 in comparison with known methods.

Further uses may include regeneration and/or rejuvenation of tissues, bones and/or cartilages. Further uses may include the treatment of diabetic neuropathic ulcers or decubitus sores; bone and cartilage damages such as deep joint cartilage or chondral damages such as surgical repair of torn tendons; arthritis in joint caused by traumas or by aging; rotator cuff disorders; non-healing wounds such as non-healing wounds such as vasculitis induced wounds, for example in lower equine limb; periodontal diseases; implant surgery; cardiovascular, thoracic, transplantation, head and neck, oral, gastrointestinal, orthopedic, neurosurgical, and plastic surgery; mesotherapy and/or mesotherapy injections; cardiac muscle damages such as in chronic cardiac failure, heart failure, ischemic and non- ischemic disorders, cardiomyopathy; gastro-oesophageal reflux disease; anal or urinary incontinence; facial surgery such as facial surgery induced alopecia (alopecia due to hair follicle loss in the side burn areas), hair loss, alopecia, face-lift surgery (rhytidectomy), rhinoplasty, dermal fat grafts (in the treatment of facial augmentation, congenital hemiatrophy of the face such as congenital cartilage nose atrophy and lipoatrophy such as in HIV/AIDS suffering patients, genital dysfunction, erosion and arthroscopy); wound healing complications such as after eyelid blepharoplasty; corneal disorders such as corneal opacity such as those caused by chemical burns, affliction by Steven's Johnson syndrome and corneal ulcers; scarring of the cornea; dry eye syndrome; haematological diseases such as Thalassaemia; peripheral nerve damage, nerve suture and spinal cord injury; bone defects or disorders such as bone graft or bone fracture, skin damages or disorders such as acne (especially after dermabrasion treatment), burns, rubella or small pox scars, vitiligo, lipoatrophy, Kaposi's sarcoma, skin skeloids or Dupuytren's palmar fibromatosis.

Further uses may include tissue healing, including bone regeneration and repair, mitogenesis, angiogenesis and/or macrophage activation.

Further uses may particularly include haemostasis, the regeneration, revitalization, hydration and/or stimulation of tissue, as biological glue, bioadhesive sealant or biological filler.

Further uses may particularly include wound care, surgery, injections for orthopedic and injections for esthetic, cosmetic or volume corrections.

Further uses may include the regeneration and/or rejuvenation of skin tissues, particularly in promoting and/or initiating skin regeneration such as reducing skin wrinkles, deep wrinkles, acne (especially after dermabrasion treatment), burns, rubella or small pox scars, vitiligo and lipoatrophy (e.g. anti-aging compositions and skin regeneration compositions), amelioration of nasolabial lines and treatment of skin damages or disorders such as skin burns, Kaposi's sarcoma, skin skeloids or Dupuytren's palmar fibromatosis, in the reduction of pain associated with skin and tissue regeneration, for hemorrhoidal cushion, erectile dysfunction, caverna, cavernosal fibrosis, lapeyronie's disease, vagina and/or labia.

Further uses may include wound or tissue healing, regeneration treatments or sports medicine for the knee, elbow, (torn) muscles, spine, spinal disc, tendon, ligament, the treatment of traumatic or surgical wounds such in the fitting and/or holding and/or sealing of native or prosthetic grafts (especially skin, bone grafts and/or dental prostheses or implants or the like, including also the graft donor site); treatment of arthritis, osteoarthritis, gonarthritis, tendinitis, rotator cuff, treatment of vasculitis; ulcers such as diabetic neuropathic ulcers or decubitus sores; radiodermatitis (e.g. after irradiation on an epidermoidal skin carcinoma) and closing fistulas (such as for cyclists).

Further uses may include the treatment of cardiac disorders, cardiac regeneration such as in the treatment of heart failure, chronic cardiac failure, ischemic and non-ischemic cardiac failure and cardiomyopathy.

Further uses may include the treatment of urinary and/or anal incontinence.

Further uses may include the treatment of reflux oesophagitis and/or gastro-oesophageal reflux disorder.

Further uses may include the treatment of skin damages such as in skins damaged by radiations (radiodermatitis or sun damaged skin), aged skins or burned skins and/or in the amelioration of facial wrinkles, rhytids, acne (especially after dermabrasion treatment), burns, rubella or small pox scars, vitiligo, lipoatrophy or lipodystrophy, Kaposi's sarcoma, skin skeloids or Dupuytren's palmar fibromatosis and/or in skin rejuvenation treatments.

Further uses may include the treatment of lipoatrophy such as in HIV/AIDS patients and in other congenital hemiatrophy of the face such as congenital cartilage nose atrophy. Further uses may include the treatment of bone, cartilage and articular disorders such as chondral damage, arthritis, osteoarthritis, cartilage and/or bone injury such as deep cartilage damage and/or erosion and/or arthroscopy, tendon torn and rotator cuff in shoulder.

Further uses may include the treatment of hematological diseases such as Thalassaemia.

Further uses may include the treatment of corneal disorders such as dry eye syndrome; corneal opacity such as those caused by chemical burns, affliction by Steven's Johnson syndrome; scarring of the cornea and corneal ulcers.

Further uses may particularly include the treatment of peripheral nerve damage, Schwann cell damage, glial cell damage, neurons damage, nerve suture and spinal cord injury.

Further uses may particularly include the treatment of type I diabetes, insulin-dependent diabetes and/or hyperglycaemia.

Further uses may include the treatment of bone defects or disorders such as bone graft or bone fracture.

The use of the resulting composition of the invention can be further modified before application and according to the therapeutic objective.

Compositions of the invention can be used together with bone filling materials, especially resorbable filling materials such as hydroxyapatite (calcium phosphate ceramic used as a biomaterial) or demineralised bone, or used as a mixture with bone extracts in a process for the regrowth of bone for example in craniofacial and orthopaedic procedures.

Further uses may include orthopaedics for example as visco-supplementation or for bone reconstruction using a combination of the present formulations with stem cells, cell extract and/or TCP.

Further uses may include as wound sealant in plastic surgery including burn grafting and other free skin graft applications, for example in oncology for favouring tissue regeneration, including speeding (neo)vascularization. Further uses may include in wound healing treatments at the skin graft donor site.

Further uses may include wound care as biological glue, for example for burns or diabetic ulcers.

Further uses may particularly include the treatment of chronic wounds that may lack sufficient blood circulation to facilitate the wound healing cascade.

Further uses may include the treatment of periodontal disease where a loss and/or a damage of the periodontal tissues is observed, such a treatment comprising for example placing at the periodontal site or cavity in a human or a lower animal in need of periodontal tissue regeneration a composition according to the invention.

Further uses may include eliminating or greatly reducing post-operative bleeding and extravasation or loss of serous or other fluid in these applications, reducing the infection risk caused by most bacteria and/or enhances connective tissue formation compared to natural healing (i.e. no exogenous agents added) or improve healing obtained through the use of other platelet concentrates, PRP compositions prepared with known methods.

Further uses may particularly include promoting and/or initiating wound healing and/or tissue regeneration or for the preparation of cosmetic compositions for skin regeneration such as reducing skin wrinkles, acne (especially after dermabrasion treatment), rubella or small pox scars, vitiligo and lipoatrophy (e.g. anti-aging compositions and skin regeneration compositions).

The compositions obtained by a container, syringe, tube or medical device according to the invention, manufacturing processes of the present invention may be administered locally or injected in the wound or in or near to the grafted organ or injected subcutaneously. Local administration may be by injection at the site of injury or defect or by insertion or attachment of a solid carrier at the site, or by admixture with a cream or emulsion, or by inclusion in a tissue or paper or hydrogel carrier, or by direct, topical application of the composition of the invention such as in the form of eye drops. Preferably, the compositions are readily syringable compositions. The mode of administration, the dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

The compositions of the invention may be administered in combination with a co-agent useful in the treatment of tissue regeneration such as a healing agent, a wrinkle filler, an anti-aging agent such as an anti-aging vitamin complex, an antibacterial agent, antibiotic agent, an corticosteroid agent, an antalgic and analgesic agent, or an anesthetic agent like adrenaline, etc... The compositions obtained by the manufacturing processes of the present invention may be combined with a co-agent useful in the treatment of tissue regeneration for simultaneous, separate or sequential use in tissue regeneration therapy such as wound healing, bone and periodontum growth repair.

Further uses may include therapeutic use, particularly as autogenous biological glue in a haemostatic system intended to accelerate the physiological process of tissue regeneration, for example in dental implantology, skin and bone surgery, cartilage and tendon surgery, orthopedics, corneal and peripheral nerve regeneration and cardiac surgery. Further uses may particularly include cosmetic use, particularly as autogenous rejuvenation material intended to be used for example as wrinkle, scar or fat deficiency filler, alone on in combination with at least one anti-aging agent.

Further uses may particularly include the acceleration and/or promotion of the healing process of wounds, even chronic unhealing wounds, leading to successful closures where weeks of conventional therapies had failed and achieving a decrease in infection risks, an improvement in patient's recover and comfort, a reduction of medical care costs and a better esthetic final result.

The compositions, containers, tubes or syringes of the invention may also use plasma derived from several identified donors. The invention is not limited to autologous biological materials, such as collection of concentrated platelets from the wounded own biological material. The invention encompasses the use of biological materials obtained from one or more third parties, who need not be of the same species as the patient whose wound is being treated with the compositions described herein unless bio-incompatibility would result from the use of such third party biological materials.

Further uses may include sealing a surgical wound by applying to the wound a suitable amount platelet concentrate, BMC composition, PRP composition, A-PRP composition once it has begun to gel. Moreover, due to the high quality standards in place for the manufacturing process and to the fact that the wound or tissue healant compositions may be prepared solely from blood components derived from the patient that is to receive the wound or tissue healant compositions there is a zero probability of introducing a new blood transmitted disease to the patient.

A wide variety of drugs or proteins with other biologic activities may be added to the compositions herein described. Examples of the agents to be added to the compositions (for example prior to the addition of the serum) include, but are not limited to, analgesic compounds, antibacterial compounds, including bactericidal and bacteriostatic compounds, antibiotics (e.g., adriamycin, erythromycin, gentimycin, penicillin, tobramycin), antifungal compounds, anti-inflammatories, antiparasitic compounds, antiviral compounds, enzymes, enzyme inhibitors, glycoproteins, growth factors, recombined (e.g. lymphokines, cytokines), hormones, steroids, glucocorticosteroids, immunomodulators, immunoglobulins, minerals, neuroleptics, proteins, peptides, lipoproteins, tumoricidal compounds, tumorstatic compounds, toxins and vitamins (e.g., Vitamin A, Vitamin E, Vitamin B, Vitamin C, Vitamin D, or derivatives thereof). It is also envisioned that selected fragments, portions, derivatives, or analogues of some or all of the above may be used.

In one embodiment, compositions herein described can be admixed with a coagulation activator, thrombin serum, tricalcium phosphate (TCP), a bone substitute, hyaluronic acid composition, calcium gluconate, calcium saccharate, chitosan, fibroins, silk protein or fibroin-fibroin proteins, growth factors, mannitol, collagen, albumin, ascorbic acid, cream, fat cells, fat tissue, bone marrow concentrate, lubricin, cd-gelatin, botulinum toxin and/or one or more cell extracts. Such substances may be combined during the preparation of the hematology tubes or syringes (via for example an injector) or after the preparation of the hematology tubes or syringes as herein described.

Biomaterials that may be used in any aspect or embodiment of the present invention may be selected from, Synthetic degradable polymers, Polylactides/glycolides, Polycaprolactone, Polyhydroxyalkanoates, Poly(propylene fumarates), Polyurethanes, Natural biopolymers, Proteins, Collagen, Elastin, Fibrin/fibrinogen, Silk protein or fibroin, Polysaccharides, Alginates, Chitosan, Hyaluronic acid, Bioactive ceramics, Calcium phosphates, Bioactive glasses, Composites, Synthetic polymers/bioactive ceramics, Biopolymers/bioactive ceramics, Tissue derived ECM, Small intestine submucosa, Skin extracellular matrix, agar, mannitol, albumin, gelose and/or collagen. Preferred biomaterials are hyaluronic acid, chitosan, silk protein, fibroin and polylactides. Such biomaterials may be used instead of hyaluronic acid or in combination with hyaluronic acid.

Compositions obtained in accordance with any of the method claims of the present invention or containers or syringues of the present invention may also comprise or be prefilled with Relaxin, Alginate, Histatins, Vascular endothelial growth factor (VEGF), Avotermin (recombinant, active, human TGFbeta3), Bilayer skin equivalent (GG-EGF/TEECM), Lipido-colloid dressings (Urgotul), Liposomes containing natural flavonoid dihydroquercetin, phospholipid lecithin, and zwitterionic amino acid glycine, Cepan Cream, Intralesional triamcinolone acetonide (TAC), Propranolol, Coenzyme Q10 (CoQ10), 2-[4-(2,4-dimethoxy-benzoyl)-phenoxy]-1-[4-(3-piperidin-4-yl-propyl)-piperidin-1-yl]-ethanone derivatives, Collagen, percutaneous, Chitosan-dextran derivative gel, Verbena officinalis L., Linoleic fatty acid emulsion, Corpitol Emulsion, Carica candamarcensis, Flivasorb dressings with superabsorbent particles, Stryphnodendron polyphyllum Mart. and Stryphnodendron obovatum Benth, citrus reticulata blanco extract, onion extract, Contractubex gel, Petrolatum-based ointment, Bischofit-based ointment, Silver foam dressing UrgoCell Silver, Plasma skin regeneration (PSR), Sparassis crispa (SC) as a medicinal mushroom, Topoisomerase I inhibitor camptothecin (CPT), trolamine-containing topical emulsion (Biafine), Mimosa pudica, Roots of Arnebia densiflora (Nordm.) Ledeb. (Boraginaceae), Iodine, 10-hydroxycamptothecin (HCPT), Glycerol Trinitrate (GTN) ointment, Substance P (SP), Ozonated olive oil, Acacia honey, Atropa belladonna L. (AB) aqueous extract, Lobaria pulmonaria (L.) Hoffm, Pteleopsis suberosa Engl. et Diels n-butanol fraction, Drimys angustifolia Miers. (Winteraceae), Cordia verbenacea.Mitomycin C (MMC), 5-fluorouracil, imiquimod 5% cream, Panax notoginseng.

Advantages rely in yields obtained with predictability, higher volume of resulting composition, entirely closed circuit system and/or automatic transfer of PRP/BMC into biomaterial tube or syringe.

What is claimed is:

1. A container for preparation of any of plasma concentrate (PC) and bone marrow concentrate (BMC) in combination with at least one biomaterial, wherein the container is prefilled with the at least one biomaterial and at least one coagulation activator prior to introduction of blood or bone marrow for concentrate formation, wherein the container is sterile and under vacuum with the at least one biomaterial and at least one coagulation activator prefilled therein prior to use, wherein the at least one biomaterial is selected from hyaluronic acid, chitosan, silk protein or fibroin, cell extract, or any combination thereof, and wherein the at least one coagulation activator is selected from thrombin serum, calcium gluconate, calcium chloride, or any combination thereof.

2. The container of claim 1, wherein the at least one coagulation activator comprises a thrombin activator, a fibrinogen activator, thrombin, an autologous thrombin, an autologous thrombin serum, calcium chloride, calcium gluconate, calcium saccharate, or a combination thereof.

3. The container of claim 2, wherein the calcium gluconate comprises about 1% to about 10%.

4. The container of claim 2, wherein for a 100 ml of solution, the calcium gluconate comprises about 9.5 g and the calcium saccharate comprises about 360 mg.

5. The container of claim 2, wherein for a 2 ml single dose ampoule, the calcium gluconate comprises about 0.19 g and the calcium saccharate comprises about 7.2 mg for a calcium content of about 0.463 mmol per 2 ml ampoule.

6. The container of claim 2, wherein for a 5 ml single dose ampoule, the calcium gluconate comprises about 0.47 g and the calcium saccharate comprises about 18 mg for about 1.148 mmol per 5 ml ampoule.

7. The container of claim 1, wherein the container is prefilled with at least one anticoagulant.

8. The container of claim 7, wherein the at the least one anticoagulant comprises about 0.2 ml to about 1 ml of anticoagulant.

9. The container of claim 7, wherein the at least one anticoagulant comprises sodium citrate.

10. The container of claim 1, wherein the container is prefilled with any of a filter and a composition allowing separation of red blood cells (RBCs).

11. The container of claim 10, wherein the composition comprises a cell selector gel (CSG), a thixotropic gel, an inert polyester CSG, or a combination thereof.

12. The container of claim 11, wherein the container comprises about 1 ml to about 4 ml of cell-selector gel.

13. The container of claim 1, wherein the container contains from about 0.5 ml to 5 ml of the at least one biomaterial.

14. The container of claim 1, wherein the hyaluronic acid is in the form of a gel.

15. The container of claim 14, wherein the hyaluronic acid resides in a buffer.

16. The container of claim 15, wherein the hyaluronic acid comprises a phosphate buffer containing sodium chloride, dipotassium hydrogenphosphate, potassium dihydrogenphospate, potassium chloride, water, or a combination thereof.

17. The container of claim 1, wherein the hyaluronic acid is reticulated or non-reticulated.

18. The container of claim 1, wherein the hyaluronic acid comprises about 40 mg to about 200 mg.

19. The container of claim 1, wherein the hyaluronic acid has a molecular weight of about 1000 KDa to about 2000 KDa at about 1.5% to about 2.5% concentration.

20. The container of claim 1, wherein the container is a centrifugation tube and is prefilled with a thixotropic gel and an anticoagulant.

21. The container of claim 20, wherein the tube is prefilled with about 2.0 g of hyaluronic acid 1550 KDa, about 1.9 g of thixotropic gel, and about 0.7 ml sodium citrate solution at about 0.109M.

22. The container of claim 1, wherein the container comprises at least one PC or BMC preservation solution.

23. The container of claim 22, wherein the least one PC or BMC preservation solution comprises plasmalyte-A.

24. The container of claim 1, wherein the container comprises a cell selector gel, tricalcium phosphate (TCP), a bone substitute, hyaluronic acid composition, calcium gluconate, calcium saccharate, chitosan, fibroin, fibroin-silk protein or fibroin proteins, growth factors, mannitol, collagen, albumin, ascorbic acid, cream, fat cells, fat tissue, bone marrow concentrate, lubricin, cd-gelatin, botulinum toxin, one or more cell extracts, or a combination thereof.

25. The container of claim 24, wherein the container comprises an autologous cell extract selected from an extract of keratinocytes, bone marrow, fibroblasts, periosteum or corneal cells, melanocytes and Langerhans cells, fat cells, muscle cells comprising any of myoblasts and satellite cells, osteoblasts, chondrocytes, umbilical cord cells, stem cells, mesenchymal stem cells (MSCs), preadipocytes, adipocytes, pre-endhotelial cells, Schwann cells or Achilles tendon cells, or a combination thereof.

26. The container of claim 1, wherein the container comprises any of a tube and syringe.

27. The container of claim 26, wherein the container comprises a tube or syringe that is adapted to allow for the collection or withdrawal of about 1 ml to about 20 ml of whole blood, bone marrow, PC or BMC.

28. The container of claim 1, wherein the container is under vacuum.

29. The container of claim 1, wherein the container is any of sterile and non-pyrogenic, wherein the container is adapted for preparation of platelet rich plasma (PRP), autologous PRP, PC, autologous PC, autologous BMC, or a combination thereof.

30. A kit for preparation of any of plasma concentrate (PC) and bone marrow concentrate (BMC) in combination with at least one biomaterial selected from hyaluronic acid, chitosan, silk protein or fibroin, cell extract, or any combination thereof, wherein the kit comprises:

a container, wherein the container is prefilled with the at least one biomaterial and at least one coagulation activator prior to introduction of blood or bone marrow for concentrate formation, wherein a prefilled combination of biomaterial and coagulation activator enhances stability of a resulting biomaterial-PC/BMC composition formed after introduction of the blood or bone marrow into the container, wherein the container is sterile and under vacuum with the at least one biomaterial and at least one coagulation activator prefilled therein prior to use, and wherein the at least one coagulation activator is selected from thrombin serum, calcium gluconate, calcium chloride, or a combination thereof; and a collection device to be affixed to the container for collecting any of blood and bone marrow into the container.

31. The kit of claim 30, wherein any of the blood and the bone marrow is collected in closed circuit.

* * * * *